United States Patent [19]

Maris

[11] Patent Number: 5,706,094
[45] Date of Patent: Jan. 6, 1998

[54] ULTRAFAST OPTICAL TECHNIQUE FOR THE CHARACTERIZATION OF ALTERED MATERIALS

[75] Inventor: Humphrey J. Maris, Barrington, R.I.

[73] Assignee: Brown University Research Foundation, Providence, R.I.

[21] Appl. No.: 519,666

[22] Filed: Aug. 25, 1995

[51] Int. Cl.⁶ .......................... G01N 21/00; G01N 21/55
[52] U.S. Cl. ........................................... 356/432; 356/445
[58] Field of Search ..................... 356/432, 445

[56] References Cited

U.S. PATENT DOCUMENTS

| | | | |
|---|---|---|---|
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |

OTHER PUBLICATIONS

"Studies of High–Frequency Acoustic Phonons Using Picosecond Optical Techniques", H.J. Maris, et al., Phonon Scattering in Condensed Matter 5, Eds. A.C. Anderson, J.C. Wolfe, Springer, Berlin, 1986, p. 374, (no month available).

"Picosecond Photoinduced Electronic And Acoustic Effects In a–Si:H Based Multilayer Structures", H.T. Grahn, et al., Journal of Non–Crystalline Solids 97&98 (1987) pp. 855–858 (no month available).

"Picosecond Acoustics As A Non–Destructive Tool For The Characterization Of Very Thin Films", C. Thomsen, et al., Thin Solid Films, 154 (1987) pp. 217–223 (no month available).

"Time–resolved study of vibrations of a–Ge:H/a–Si:H multilayers", H.T. Grahn, et al. Physical Review B, vol. 38, No. 9, Sep. 15, 1988, page no. not available.

"Picosecond Ultrasonics", Holger T. Grahn, et al., IEEE Journal of Quantum Electronics, vol. 25, No. 12, Dec. 1989, pp. 2562–2569.

(List continued on next page.)

*Primary Examiner*—Frank G. Font
*Assistant Examiner*—Amanda Merlino
*Attorney, Agent, or Firm*—Perman & Green, LLP

[57] ABSTRACT

Disclosed herein is a method and a system for non-destructively examining a semiconductor sample (30) having at least one localized region underlying a surface (30a) through into which a selected chemical species has been implanted or diffused. A first step induces at least one transient time-varying change in optical constants of the sample at a location at or near to a surface of the sample. A second step measures a response of the sample to an optical probe beam, either pulsed or continuous wave, at least during a time that the optical constants are varying. A third step associates the measured response with at least one of chemical species concentration, chemical species type, implant energy, a presence or absence of an introduced chemical species region at the location, and a presence or absence of implant-related damage. The method and apparatus in accordance with this invention can be employed in conjunction with a measurement of one or more of the following effects arising from a time-dependent change in the optical constants of the sample due to the application of at least one pump pulse: (a) a change in reflected intensity; (b) a change in transmitted intensity; (c) a change in a polarization state of the reflected and/or transmitted light; (d) a change in the optical phase of the reflected and/or transmitted light; (e) a change in direction of the reflected and/or transmitted light; and (f) a change in optical path length between the sample's surface and a detector.

71 Claims, 12 Drawing Sheets

OTHER PUBLICATIONS

"Nondestructive Testing of Microstructures by Picosecond Ultrasonics" H.N. Lin, et al., Journal of Nondestructive Evaluation, vol. 9, No. 4, 1990, pp. 239–246.

"Photon Attenuation and Velocity Measurements in Transparent Materials by Picosecond Acoustic Interferometry", H.N. Lin, et al. Journal of Applied Physics, vol. 69, p. 3860 (Apr. 1991).

"Attenuation of longitudinal–acoustic phonons in amorphous $SiO_2$ at frequencies up to 440 $GH_z$", T.C. Zhu, et al., The American Physical Society 1991, pp. 4281–4289.

"Detection of Titanium Silicide Formation And Phase Transformation by Picosecond Ultrasonics", H.N. Lin, et al., Mat. Res. Soc. Proc. Advanced Metalization and Processing for Semiconductor Devices III, vol. 260, p. 221 (1992).

"Ultrasonic Experiments At Ultra–High Frequency With Picosecond Time–Resolution", H.N. Lin, et al., IEEE Ultrasonics Symp 1990, page nos. not available.

"Picosecond Optics Studies Of Vibrational And Mechanical Properties of Nanostructures", H.J. Maris, et al., AMD–vol. 140, Acousto–Optics and Acoustic Microscopy ASME 1992, pp. 134–148.

"Picosecond optical studies of amorphous diamond and diamondlike carbon: Thermal conductivity and longitudinal sound velocity", Christopher J. Morath, et al, J. Appl. Phys., vol. 76, No. 5, Sep. 1, 1994, p. 2636.

"Study of vibrational modes of gold nanostructures by picosecond ultrasonics", H.N. Lin, et al., J. Appl. Phys. vol. 73, No. 1, Jan. 1, 1993, pp. 37–45.

"Nondestructive detection of titanium disilicide phase transofrmation by picosecond ultrasonics", H.H. Lin, et al., Applied Physics Letters, No. 61, p. 2700, 1992.

"Surface Generation and Detection of Phonons By Picosecond Light Pulses" C. Thomsen et al. Physical Review B. vol. 34, No. 6, Sep. 15, 1986, The American Physical Society, pp. 4129–4138.

"Sound Velocity and Index of Refraction of AlAs Measured By Pico–second Ultrasonics", H.T. Grahn, et al. Appl. Phys. Lett. 53(21), Nov. 21, 1988 pp. 2023–2024.

"Elastic Properties of Silicon Oxynitride Films Determined by Pico–second Acoustics" by H.T. Grahn et al., Appl. Phys. Lett. 53 (23), Dec. 5, 1988, pp. 2281–2283.

"Noninvasive picosecond ultrasonic detection of ultrathin interfacial layers: CFx at the Al/Si interface" by G. Tas, R. J. Stoner and H.J. Maris, Appl Phys. Lett. 61 (15). Oct. 12, 1992 pp. 1787–1789.

"Detection Of Thin Interfacial Layers By Picosecond Ultrasonics" by G. Tas, R.J. Stoner J. Maris, G.W. Rubloff, G.S. Oehrlein and J.M. Halbout, Mat. Res. Soc. Symp. Proc. vol. 259 1992 Materials Research Society, pp. 231 236 (no month available).

W. Lee Smith et al. "Ion implant monitoring with thermal wave technology". Appl. Phys.Lett.. vol. 47. No. 6, Sep. 15, 1985. pp. 584–586.

J. Opsal et al. "Thermal and plasma wave depth profiling in silicon", Appl. Phys. Lett. vol. 47 No. 5 , Sep. 1, 1985. pp. 498–500.

A. Rosencwaig et al. "Thin–film thickness measurements with thermal waves". Appl. Phys. Lett., vol. 43 No. 2, Jul. 15, 1983. pp. 166–168.

A. Rosencwaig et al. "Detection of thermal waves through optical reflectance". Appl. Phys. Lett., vol. 46 No. 11, Jun. 1, 1985. pp. 1013–1015.

A. Elci et al. "Physics of Ultrafast Phenomena in Solid State Plasmas". Solid–State Electronics, vol. 21, 1978, pp. 151–158 (no month available).

D.H. Auston et al. "Picosecond Spectroscopy of Semiconductors". Solid–State Electronics, vol. 21, 1978, pp. 147–150 (no month available).

D. H. Auston et al. "Picosecond Ellipsometry of Transient Electron–Hole Plasmas in Germanium". Physical Review Letters, vol. 32 No. 20. May 20, 1974 pp. 1120–1123.

R.J. Stoner et al. "Kapitza conductance and heat flow between solids at temperatures from 50 to 300K". Physical Review B, vol. 48, No. 22, Dec. 1, 1993 pp. 16 373–16 387.

R.J. Stoner et al. "Measurements of the Kapitza Conductance between Diamond and Several Metals". Physical Review Letters, vol. 68 No. 10, Mar. 9, 1992 pp. 1563–1566.

S. Sumie et al. "A New Method of Photothermal Displacement Measurement by Laser Interferometric Probe". Jpn. J. Appl. Phys. vol. 31 Pt. 1, No. 11, 1992 pp. 3575–3583 (no month available).

S. Sumie et al. J.Appl. Phys. 76(10), Nov. 15, 1994 pp. 5681–5689.

F.E. Doany et al. "Carrier lifetime versus ion–implantation dose in silicon on sapphire". Appl. Phys. Lett. 50(8), Feb. 23, 1987 pp. 460–462.

D.A. Young et al. "Heat Flow in Glasses on a Picosecond Timescale". Dept. of Engineering, Brown University, Providence, RI. 1986. pp. 49–51 (no month available).

ULTRAFAST OPTICAL TECHNIQUE FOR THE CHARACTERIZATION OF ALTERED MATERIALS

This invention was made with government support under grant number DEFG02-ER45267 awarded by the Department of Energy. The government has certain rights in the invention.

FIELD OF THE INVENTION

This invention relates generally to a method and apparatus for characterizing a sample using electromagnetic radiation and, in particular, relates to a system for determining at least one characteristic, such as a density of an implanted chemical species or a density of crystalline defects within a sample.

BACKGROUND OF THE INVENTION

A significant amount of research is currently being directed to the development of non-destructive techniques for the examination and evaluation of the properties of materials. Of particular interest herein is the characterization of materials in which ions have been introduced into a region near to a surface of the material by means of implantation or in-diffusion.

In the semiconductor industry certain materials such as silicon, germanium, and gallium arsenide are frequently doped with impurities so as to change their electrical or mechanical properties. These impurities may be introduced by means of ion implantation or by means of in-diffusion from a solid, liquid or gas source. Associated with the introduction of such impurities is an amount of crystalline damage whose characteristics depend on the method by which they are introduced (e.g. energy, flux, temperature, or concentration gradient). A variety of ions are commonly used for this purpose including B, P, Ga, Ge, F, Si, B11, BF2, Sb, In, As and hydrogen. In the case of implantation, these ions are accelerated to an energy which may be as low as a few keV or as high as several hundred keV, and are then directed at the surface of the material. After entering the material an ion loses energy by collisions with the atoms of the material. These collisions result in damage to the material, such as displacements of atoms from their normal crystalline positions. For sufficiently high ion doses parts of the material may become amorphous rather than crystalline. The material is thus modified as a result of the damage that occurs (also referred to as the generation of defect sites) and as a result of the introduction of the ions themselves, even if no damage occurs. For in-diffused species, crystal damage in the sample, such as a substrate, may occur as the diffusing atoms displace sample atoms from their lattice sites. The extent of the damage depends on the size of the sample and the diffusing atoms, the nature of the diffusion source (solid, liquid, gas), the concentration of diffusion species in the source, and the details of the thermal process used to drive them into the substrate. It is also possible for there to be no crystal damage (e.g. if the diffusing atoms are small compared to the lattice constant of the sample). In such cases, diffusing atoms may occupy interstitial sites in the sample, and so may alter the local electronic and optical characteristics of the sample.

The material modification generally occurs in a surface layer or region the depth of which can vary from less than 100 Angstroms for low energy ions to several microns (e.g. when high energy ions are used). The dosage, i.e. the number of ions introduced per unit area of the surface of the material, can be varied over a wide range for implanted species by controlling the ion beam current and the time for which the ion beam is directed at the material. For the in-diffusion case the dosage can be controlled by varying the thermal cycle or the source concentration. Currently in the semiconductor industry, implant doses as low as $10^{10}$ ions per $cm^2$ and as high as $10^{18}$ ions per $cm^2$ are used for different purposes. Both the material damage and the introduction of the ions results in a change in the electrical properties of the material in the vicinity of the surface where the ions are introduced. Some of the damage to the crystalline structure can be removed by thermal annealing the material after ion implanting.

In the fabrication of semiconductor chips, ion implantation or in-diffusion may be used at a number of stages of the process. Typically, an implant is restricted to predetermined areas, i.e. the implant is patterned. Similarly, in-diffused species may be added in a pattern by masking regions with an impenetrable, heat resistant layer such as $SiO_2$ or nitride. It is important to be able to monitor the dosage and to confirm that the correct regions have been implanted or doped by in-diffusion. Since these regions may be very small, it is important for a measurement technique to have very high spatial resolution. Also, and to avoid unintentionally contaminating the sample during the measurement, it is desirable that a non-contact measurement method be used.

A number of different techniques have been used or proposed for the evaluation of ion-implanted materials, including Rutherford back-scattering, Raman spectroscopy, and sheet resistance measurements. Some of these techniques have also been used to characterize samples to which foreign atoms have been introduced by in-diffusion.

Yet another technique which has been used to characterize ion implants employs a 100% intensity modulated laser beam with modulation frequency $\omega$ that is directed at a semiconductor surface, as described by Opsal et al., "Method and Apparatus For Evaluating Surface and Subsurface Features in a Semiconductor", U.S. Pat. No. 4,854,710. The light that is absorbed in the sample generates an electron-hole plasma, and also a heavily damped thermal wave close to the surface of the sample. Both the plasma and the thermal wave oscillate at frequency $\omega$. These forced plasma and thermal oscillations give rise to small oscillations in the optical reflectivity of the sample which can be measured by means of a probe laser directed onto the same spot as the modulated laser. The amplitude and phase of the small oscillatory component at frequency $\omega$ arising in the intensity of the reflected probe beam depend strongly on $\omega$, and also can be affected by the presence of ion implants and related damage in the semiconductor. Thus a measurement of this oscillatory component can be used as a defect or ion implant monitor.

Reference in this regard can also be had to J. Opsal, "Method and Apparatus for Evaluating Ion Implant Levels in Semiconductors", U.S. Pat. No. 5,074,669. In this technique, both the unmodulated component of the reflected probe beam, and the component modulated at frequency $\omega$, are measured and analyzed. In all of the above described techniques the modulation frequency of the pump beam is typically below 10 MHz.

Photo-acoustic displacement measurements (PAD) have also been shown to be sensitive to ion-implant dosage, as described by S. Sumie et al., Jap. J. Appl. Phys. 35, 3575 (1992), and S. Sumie, et al., J. Appl. Phys. 76, 5681 (1994). In these experiments the acoustic displacement is periodic at a frequency of 87 kHz. The measurement is designed so that changes in optical reflectivity due to the electrons and holes excited in the material are not detected.

The optical methods mentioned above all use periodically-modulated continuous wave pump beams to excite the material. The frequency of the modulation is generally in the range below 10 MHz. However, this range of modulation frequencies can adversely impact the sensitivity of the measurement system and an ability to "profile" the impurities or damage distribution, and may also cause the system to be sensitive to surface effects.

The thermal and electrical properties of materials have also been studied using optical pulse techniques. Short light pulses (duration 100 psec or less) have been used to heat a metal film on a semiconductor dielectric substrate. A time-delayed probe pulse (duration also 100 psec or less) is used to measure the change in the optical reflectivity of the metal film, and from this change the rate at which the film cools by thermal conduction into the substrate can be determined. Reference in this regard can be had to Young et al., Heat Flow in Glasses on a Picosecond Timescale in Phonon Scattering in Condensed Matter V, edited by A. C. Anderson and J. P. Wolfe, (Springer, Berlin, 1986), p. 49; to Stoner et al., Measurements of the Kapitza Conductance between Diamond and Several Metals Phys. Rev. Lett. 68, 1563 (1992); and to Stoner and Maris, Kapitza Conductance and Heat Flow Between Solids at Temperatures from 50 to 300 K, Phys. Rev. B48, 16373 (1993).

Short light pulses have been used to excite electrons and holes in semiconductors, and the change in optical reflectivity that occurs as a result of the excited carriers has been measured with a short probe light pulse. In this regard reference can be made to Auston et al., Picosecond Ellipsometry of Transient Electron-Hole Plasmas in Germanium, Phys. Rev. Lett. 32, 1120 (1974); to Auston et al., Picosecond Spectroscopy of Semiconductors, Solid State Electronics 21, 147 (1978); and to Elci et al., Physics of Ultrafast Phenomena in Solid State Plasmas, Solid State Electronics 21, 151 (978)). This work has generally been directed towards achieving an understanding of how the electrons and holes relax and diffuse, rather than as a means for sample characterization.

In a paper entitled "Carrier Lifetime Versus Ion-Implantation Dose in Silicon on Sapphire", F. E. Doany et al., Appl. Phys. Lett. 50(8), Feb. 23, 1987 (pp. 460–462), a report is made of studies conducted on a silicon film of thickness 0.5 micron on a sapphire substrate. The authors employed 70 femtosecond pulses that were generated at a 100 MHz rate, the pump pulses are said to be chopped at a 1 kHz rate, and the probe pulses were obtained from the pump pulses. A change in reflectivity over time was obtained from a photodetector. In this experiment the excited carriers could not enter the substrate because of the large band gap of the sapphire, and hence were confined to the silicon film. Consequently, the electrons and holes were distributed approximately uniformly throughout the thickness of the silicon film, and this assumption was made in the analysis of the data by these authors. It was demonstrated that the lifetime of the excited free carriers was influenced by the implantation dose of $O^+$ ions, and that there is lack of carrier lifetime dependence above an $O^+$ implant dose of $3\times 10^{14}$ $cm^{-2}$. It is important to note that in this approach the generated heat cannot readily dissipate and the temperature of the sample can become high.

Reference is also hereby made to commonly assigned U.S. Pat. No. 4,710,030, "Optical Generator and Detector of Stress Pulses", by J. T. Tauc, H. J. Maris, and C. Thomsen, wherein a short duration pump beam is employed to optically generate a stress pulse in a sample. A probe beam is then directed to the sample so as to intercept the stress pulse.

A change in optical constants induced by the stress pulse is detected by observing the probe beam after it intercepts the stress pulse.

OBJECTS OF THE INVENTION

It is a first object of this invention to provide an improved method for the non-destructive evaluation of semiconductors through the use of at least one short light pulse to excite electrons and holes, and an optical probe to measure the resulting change in the optical constants of the semiconductor as a function of time.

It is a further object of this invention to nondestructively measure, with micron or submicron spatial resolution, a variation in density of foreign species as a function of position on a surface of a sample.

It is another object of this invention to determine the density of a foreign species at high as well as low doses, e.g., in the range $10^{10}$ $cm^{-2}$ and below up to $10^{18}$ $cm^{-2}$.

It is a further object of this invention to measure the density of a foreign species within a small area of a sample surface, for example, within a region having linear dimensions that are as small as a fraction of a micron.

It is one still further object of this invention to measure the density of a foreign species in a semiconductor material when a surface of the material is covered by a film or layer of another material, such as an oxide, nitride, or photoresist.

SUMMARY OF THE INVENTION

This invention teaches a method and a system for the characterization of ion-implanted and other materials through the use of a short pump light pulse to excite the material to be investigated, and an optical probe to examine the material a short time after the application of the pump pulse. A time-dependent change in the optical constants of the material, which may be manifested by a change in, by example, reflectivity or polarization, is measured and is associated with at least one characteristic of an introduced chemical species. By example, a change in reflectivity can be associated with the density of an implanted chemical species and/or with an energy at which the chemical species was implanted.

The method and apparatus in accordance with this invention can be employed in conjunction with a measurement of one or more of the following effects arising from a time-dependent change in the optical constants of the sample due to the application of at least one pump pulse: (a) a change in reflected intensity; (b) a change in transmitted intensity; (c) a change in a polarization state of the reflected and/or transmitted light; (d) a change in the optical phase of the reflected and/or transmitted light; (e) a change in direction of the reflected and/or transmitted light; and (f) a change in optical path length between the sample's surface and a detector.

In accordance with an embodiment of this invention the above-described and other problems are overcome and the objects of the invention are realized by a method and system for the determination of ion implant density, wherein an ultra-short optical pump pulse is used to excite electrons and holes in a semiconducting material, and wherein a second ultra-short optical probe pulse is applied to measure a time-dependent change $\Delta R(t)$ in the optical reflectivity of the semiconductor material caused by the presence of the electrons and holes. The pump light pulse has a wavelength which is optically absorbed in the semiconductor material to be examined, and an optical path is established to direct the pump pulse to a selected area of the surface.

The probe light pulse may be derived from the same light source as the pump light pulse, but is delayed in time relative to the pump pulse with, by example, a variable length optical path. Alternatively, the probe light pulse may be generated by a separate light source.

The charge carriers, i.e., electrons and holes, that are generated by the absorption of the pump light pulse are initially distributed throughout a layer of the material of thickness equal to the optical absorption length of the material. Some of these charge carriers diffuse towards the surface of the material where a previously ion implanted or diffused layer or region is located. Within the ion implanted or diffused region the charge carriers recombine with one another and/or are trapped at defect sites. For ion implants of low energy the thickness of the layer or region is only a few hundred A, and so for light in the visible or infrared range the absorption length can be much larger than the thickness of the ion implanted or diffused layer or region. The depth sensitivity of the measurement can be changed by the selection of the pump and probe wavelength(s).

In accordance with an aspect of this invention, and for an ion-implanted bulk material such as a semiconductor wafer, a resulting time-varying change (on a time scale less than 1 nsec) of the optical reflectivity of the semiconductor material is determined both by the number of defects in the ion implanted or diffused surface region and by the rate at which the charge carriers diffuse into non-implanted or diffused regions of the material.

In accordance with a further aspect of this invention a measurement of ion implant density in a semiconductor material which has a film of another material on the surface is made possible. In this case both the pump and probe light pulses are selected to have wavelengths in a range that are not significantly absorbed by the overlying surface film.

In the instant invention, rather than exciting a sample periodically at a single frequency ($\omega$), as in certain of the optical techniques described previously, a sample is preferably excited using a multiplicity of substantially independent pump pulses of very short duration (typically 1 picosecond or less). Each pump pulse is partially absorbed in the sample, which in turn induces a transient electron-hole plasma near the surface of the sample which subsequently decays through processes including recombination and diffusion into the bulk. This is accompanied by the generation of heat.

The net result of such processes is a small time-dependent change in the optical constants n and $\kappa$ (complex index of refraction) of the sample in a region close to the surface, and also a possible displacement of the surface. These changes lead to a change $\Delta R(t)$ in the optical reflectivity, a shift $\delta\phi(t)$ in the phase of the reflected or transmitted light, a change in the polarization state of the reflected light, and a change in direction of the reflected or transmitted light. These changes are dependent also on the polarization and the angle of incident of the probe light. The measured changes depend, among other things, on the detailed distribution of defects and foreign atoms near the sample's surface and in the bulk.

To measure the function $\Delta R(t)$ a pulsed probe beam can be employed to make reflectivity measurements at a series of closely spaced discrete times for a series of times ranging from zero to up to, by example, several nanoseconds following the arrival of the pulse. The effective detection bandwidth of such a transient measurement system is many thousands of times greater than can be obtained using continuous wave probe techniques such as those described previously. Accordingly, the measurement technique of this invention has an improved sensitivity to very low levels of damage or dose.

Yet another important distinguishing feature of the subject system is that a periodic generator is not required. The sample need not be continuously excited in a periodic manner, and neither plasma or thermal oscillations need be considered in the analysis of the measurements. In an embodiment of this invention the probe beam is applied as pulses, and the times at which probe pulses arrive at the sample are controlled with respect to the pump pulses. Several different techniques for implementing such a system are described herein.

In a further embodiment of this invention the probe light is applied as a continuous wave (cw) beam.

In accordance with the teaching of this invention there is provided both apparatus and methods for examining a semiconductor sample having at least one localized region underlying a surface into which a chemical species may have been introduced. A method in accordance with this invention includes a first step of inducing at least one transient time-varying change in optical constants of the sample at a location at or near to a surface of the sample. A second step measures a response of the sample to an optical probe beam, either pulsed or continuous wave, at least during a time that the optical constants are varying. A third step associates the measured response with at least one of chemical species concentration, chemical species type, implant energy, a presence or absence of an introduced chemical species region at the location, and a presence or absence of implant-related damage.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The disclosure of the above-referenced commonly assigned U.S. Pat. No. 4,710,030 is incorporated by reference herein in its entirety for teaching an electro-optic non-destructive measurement system having some components which are suitable for use in practicing this invention. As was previously described, the system of Tauc et al. uses the pump beam to generate an elastic or stress wave in the sample under test. Although the teaching of the present invention does not require the generation of an elastic or stress wave in the sample, the same laser, optical and detector components as described by Tauc et al. can be used to practice the present invention. Furthermore, the teaching of this invention can be employed in conjunction with the acoustics technique of Tauc et al., which can be of significant utility for implant evaluation.

As such, it should be noted that the teaching of this invention, as described in detail in the ensuing paragraphs, can be used in conjunction with the teaching of Tauc et al. to augment the characterization of samples, in particular the determination of at least one characteristic of a region within a semiconductor sample wherein a chemical species has been introduced by implantation or diffusion.

Also, and although described below primarily in the context of systems and methods that measure a change in reflectivity of a sample over time, it is also within the scope of this invention to employ ellipsometry, either as a primary detection method or in combination with reflectometry. By example, and as is described in U.S. Pat. No. 5,166,752, ellipsometry is an optical technique that employs polarized light. Ellipsometry can be considered as involving a measurement of tan ψ, the change in the amplitude ratio upon reflection or transmission, and Δ, the change in the phase difference upon reflection or transmission. For the case of reflection, the quantities ψ and Δ are functions of the optical constants of the surface material, the wavelength of the light used, the angle of incidence, the optical constants of the ambient medium, and for film-covered surfaces, the thicknesses and optical constants of the films.

Figure 1A:
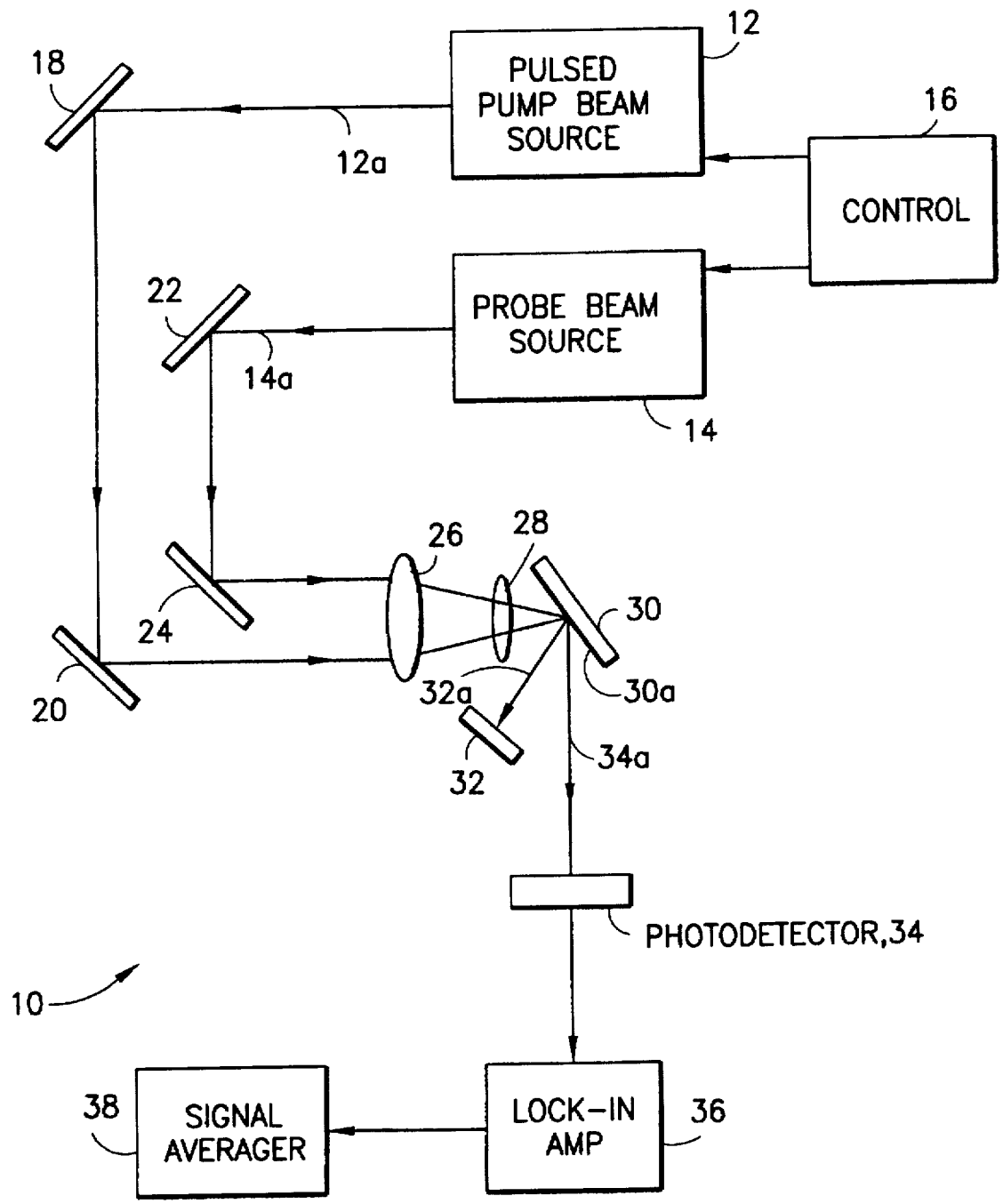
FIG. 1A is a block diagram of a first embodiment of a non-destructive, non-contact materials characterization system in accordance with this invention.
Figure 1B:
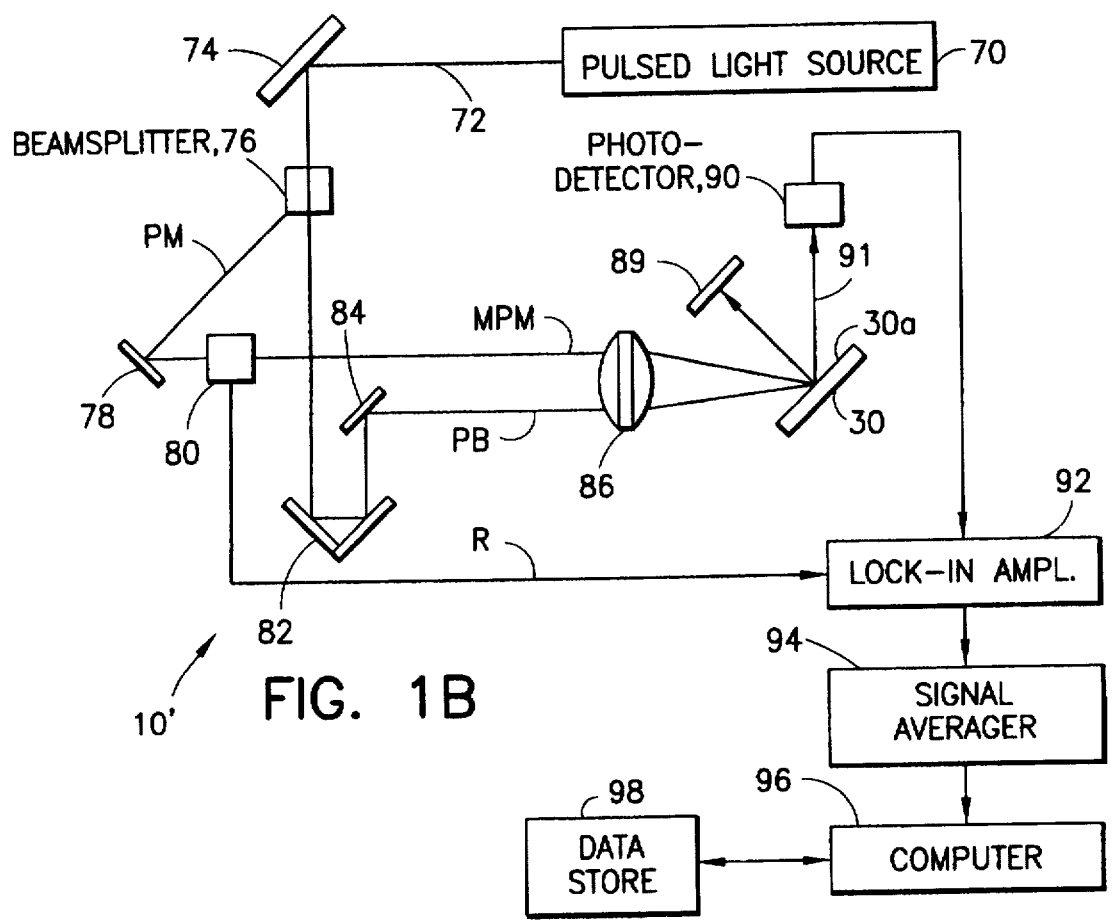
FIG. 1B is a block diagram of a second embodiment of a non-destructive, non-contact materials characterization system in accordance with this invention.
Figure 2:
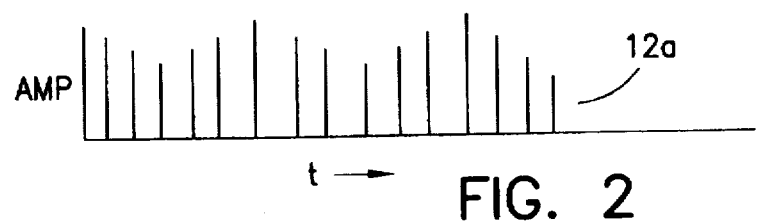
FIG. 2 illustrates a pulse train of pump beam pulses having an overlying low frequency intensity modulation impressed thereon.

Reference is made to FIG. 1A which is similar to FIG. 2 of Tauc et al (U.S. Pat. No. 4,710,030). An ion implant characterization system 10 includes a pulsed pump beam source 12 and a probe beam source 14 which are all operated by a controller 16. Although two lasers are indicated as the source of both the pump and probe pulses, it is also within the scope of the invention to employ a single laser to generate the pump and the probe optical pulses, as will be illustrated in FIG. 1B. It should be noted that wherein Tauc et al. disclose a continuous wave (cw) probe beam in the embodiment of their FIG. 2, in FIG. 1A of this patent application both the pump beam and the probe beam are preferably pulsed. However, and as will be made more apparent below, it is also within the scope of this invention to employ a cw probe beam.

A plurality of mirrors 18, 20 and 22, 24 may be employed for directing the pump and probe pulses 12a and 14a, respectively, to a focussing optical element shown schematically as a lens 26. Lens 26 provides a focussed pulsed beam 28 to a surface 30a of an ion implanted sample 30 that is being characterized. A beamblocker 32 is employed to stop any reflected portion 32a of the pump beam 12a, while a photodetector 34 (either a single detector or an area array detector) is employed to receive the reflected portion of the pulsed probe beam, i.e., the portion of the probe beam that reflects from the surface 30a of the sample 30. The photodetector 34 converts the incident reflected probe pulse 34a to an electrical signal which is coupled, preferably, to a lock-in amplifier 36 and thence to a signal averager 38. These components are employed to average a plurality of probe beam signals to improve the signal-to-noise ratio.

A second, presently preferred alternative embodiment of the invention is illustrated in FIG. 1B. This embodiment is substantially identical in form to the FIG. 3 system described in U.S. Pat. No. 4,710,030. In FIG. 1B a measurement system 10' uses a pulsed probe beam. A source beam 72, having an average power of 10 μW to 1 kW, a repetition rate of 1 Hz to 10 GHz and a duration of 0.01 psec to 100 psec, from light source 70 is directed by mirror 74 through beam splitter 76. At beam splitter 76, a portion of source beam 72 becomes pump beam PM, which is directed by mirror 78 to chopper 80. The chopper 80 imparts a modulation to pump beam PM that is several orders of magnitude longer in duration than a pulse of beam 72. Thus, chopper 80 permits a series of pump pulses to impinge upon sample 30 during one period and then blocks a series of pump pulses during the next period.

Beam splitter 76 directs a smaller portion of beam 72 to a corner cube mirror 82. The distance between mirror 84 and the corner cube 82 is varied to vary the delay between impingement of probe beam PB and pump beam PM at sample 30.

Pump beam PM and probe beam PB pass through lens 86 where they are focussed on the same spot on the surface 30a of the sample 30. The reflected portion of pump beam PM is stopped by beam-blocker 89. Detector 90 detects the change in intensity of reflected probe beam 91 as the optical constants of sample 30 vary. Lock-in amplifier 92 accepts and amplifies signals from detector 90 that match only the frequency and phase of chopper 80, as provided by reference signal R to lock-in amplifier 92. Probe beam PB is not modulated by chopper 80, as provided by reference signal R to lock-in amplifier 92, but may acquire a change in intensity according to the modulation rate. Each series of pump pulses allowed through chopper 80 induces a corresponding series of excitations in the sample 30 which in turn induce changes in the optical constants of the sample, which may be manifested as a time-dependent change in reflectivity and a corresponding change in the intensity of reflected beam 91 during each series. Alterations in intensity of reflected probe beam 91 that occur at other than the frequency of chopper 80 are rejected by amplifier 92.

Lock-in amplifier 92 provides a single voltage output proportional to the difference between the original intensity of beam 91 when sample 30 is under illumination of pump beam PB and when it is not under illumination. Signals received by lock-in amplifier 92 are averaged over time by signal averager 94 and transferred to computer 96 for storage and analysis. A part of this analysis involves a comparison of the measured data with pre-stored data obtained from reference samples, as will be described in detail below. As such, coupled to the computer 96 may be a data storage device 98 that stores reference sample data.

Figure 1C:
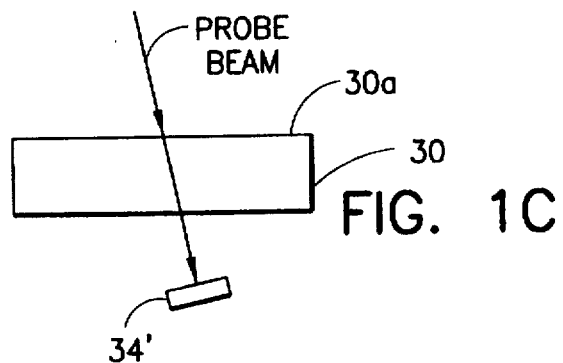
FIG. 1C illustrates a further embodiment of this invention wherein a photodetector is positioned for measuring probe light that is transmitted through a sample.

FIG. 1C illustrates an embodiment of this invention wherein a photodetector 34' is positioned for detecting probe light that is transmitted through the sample 30. The photodetector 30 can be used alone, or in combination with the embodiments illustrated in FIGS. 1A and 1B.

When employing ellipsometry, either as a primary detection method or in combination with reflectometry, the embodiments of FIGS. 1A and 1B are modified as required to include one or more suitable polarizers into the probe beam optical path, and the detection and measurement systems are also modified as required so as to detect the ellipsometric parameters $\Delta$ and $\psi$ upon a reflection of the optical probe beam. General reference in this regard may be had, by example, to the above-mentioned U.S. Pat. No. 5,166,752.

In a presently preferred embodiment of the teaching of this invention, the time-dependence of the change in optical reflectivity $\Delta R(t)$ of the reflected probe beam is of most interest. In this embodiment the magnitude and time dependence of change in the optical reflectivity is determined by the distribution of foreign species and the process(es) by which they are introduced into the sample 30.

That is, from measurements on a series of test samples it has been found by the inventor that the reflectivity change $\Delta R(t)$, for times in the range 0 to 1000 psec, is particularly sensitive to the level of the ion implant dose. It should be noted that the observed change in reflectivity is typically in the range of $10^{-3}$ to $10^{-5}$.

Figure 6A:
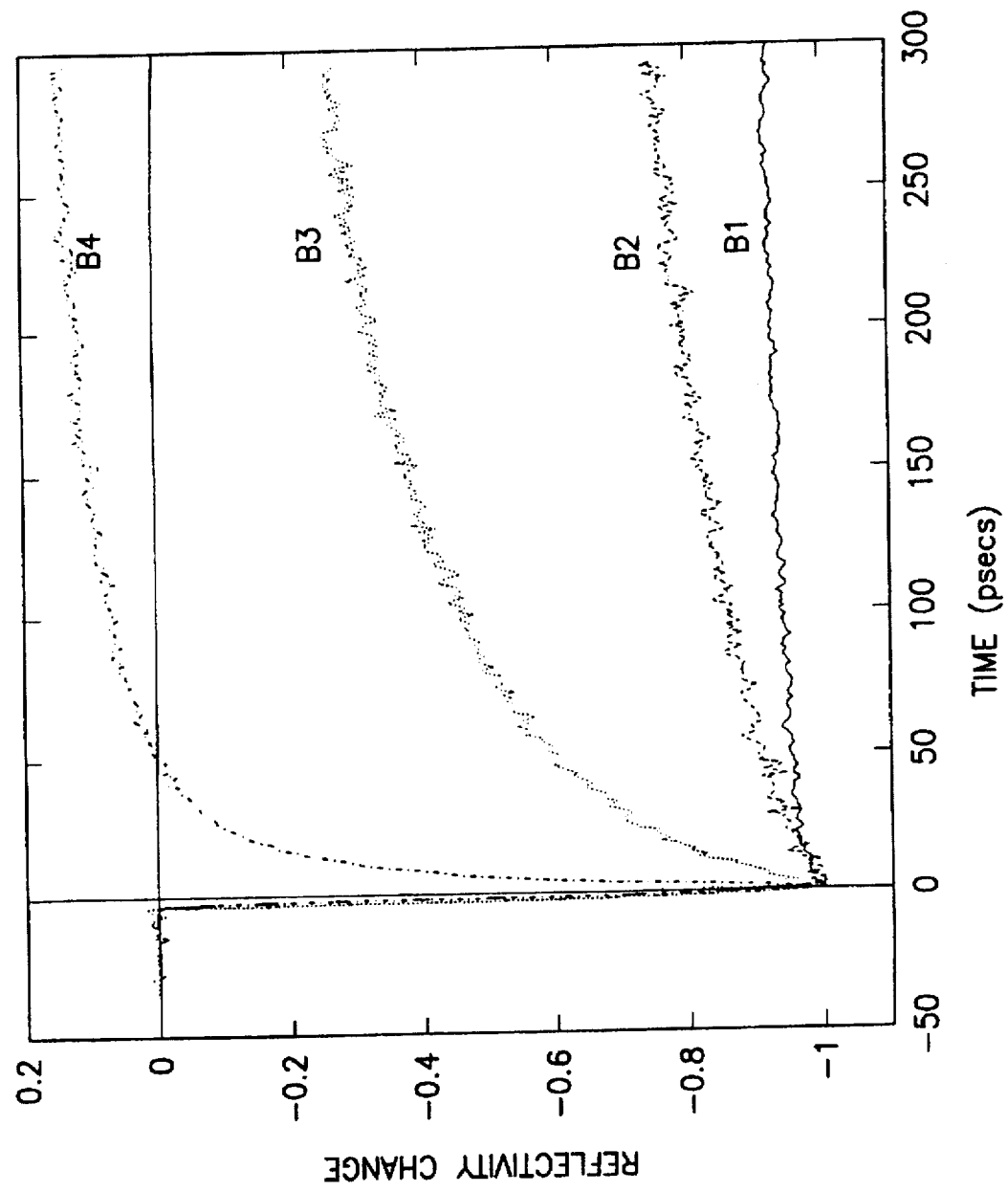
FIG. 6A is a graph illustrating a change in reflectivity over 300 picoseconds for four semiconductor samples each having different implant densities.
Figure 6B:
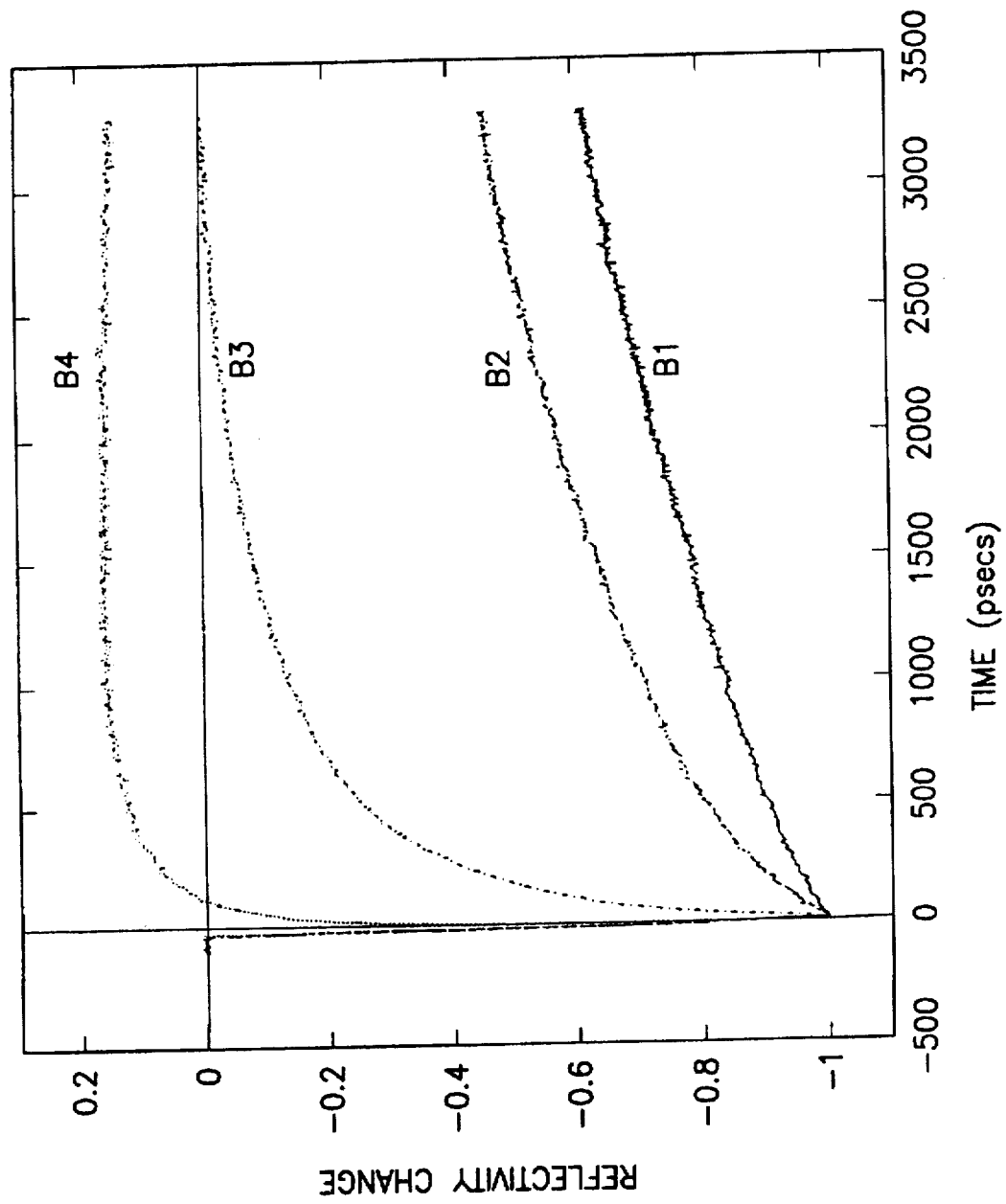
FIG. 6B is a graph illustrating the change in reflectivity over 3500 picoseconds for the four samples of FIG. 6A.

The graphs of FIGS. 6A–6B illustrate data that was obtained from four boron-implanted wafers (designed B1–B4). Each graph plots the change $\Delta R(t)$ in optical reflectivity as a function of time after the pump pulse has been absorbed in the sample ($t_0$ in FIGS. 7A and 7F). The implant energy was 40 keV for each wafer, and the dosages are shown in Table 1.

TABLE 1

| SAMPLE # | DOSE (cm$^{-2}$) |
|---|---|
| B1 | 0 |
| B2 | $5 \times 10^{10}$ |
| B3 | $5 \times 10^{11}$ |
| B4 | $5 \times 10^{12}$ |

Figure 3:
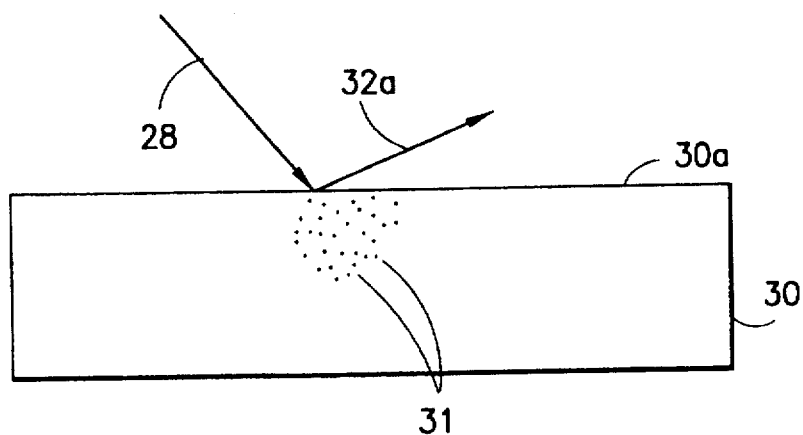
FIG. 3 is an enlarged cross-sectional view, not to scale, of a portion of a semiconductor wafer having an ion implanted region.

FIG. 3 illustrates the sample 30, comprised of a semiconductor material such as silicon, having an implanted region that underlies the surface 30a. The implanted region is comprised of implanted atoms and defect sites, shown collectively as 31. The depth of the implant region is a function of, among other factors, the mass of the implanted ion, the crystalline characteristics of the sample material, which may include overlying layers, and the implant energy.

Typical characteristics of the light pulses employed in the system 10 of FIG. 1 are as follows. The pump pulse 12a has an energy of approximately 0.001 to 100 nJ per pulse, a duration of approximately 0.01 psecs to 100 psec per pulse, and a wavelength in the range 200 nm to 4000 nm. The pulse repetition rate (PRR) is in the range of 100 Hz to 5 GHz and, as is shown in FIG. 2, the pump pulse train may be intensity modulated at a rate of 1 Hz to 100 MHz, depending on the PRR. The pump pulse 12a is focussed by lens 26 to form a spot on the sample surface 30a of diameter in the range of approximately 10 micrometers to 20 micrometers, although smaller spot sizes, and hence smaller lateral resolutions, can also be employed.

The probe beam 14a that is used to measure the reflectivity change may be derived from the same laser as the pump beam by means of a beam splitter, as in FIG. 1B, or from another laser, as in FIG. 1A. The probe pulse 14a is delayed relative to the pump pulse 12a through, by example, the use of a mechanical stage to give an additional optical path length. The output of the photodetector 34 is applied to the lock-in amplifier 36 and thence to the signal averager 38.

It should be appreciated that FIGS. 1A and 1B are but two suitable embodiments for practicing this invention. Other embodiments of this invention may employ two lasers with different wavelengths. Still other embodiments of the invention may employ two lasers with different pulse repetition rates, or a vibrating retro-reflector to vary the optical path length and hence the relative temporal position of the probe pulse with respect to the pump pulse. In other embodiments of the invention multiple fixed pump/probe delays can be employed, or continuously variable delays. In still other embodiments of this invention the pump and probe pulse beams can be applied coaxially, while in other embodiments the probe and pump beams can be applied so as to be parallel with one another. The probe and pump beams can be applied through the same or through different optical components. In other embodiments of this invention the probe and pump beams can have the same polarization or may have different polarizations. In other embodiments of this invention the probe and pump beams can have the same angle of incidence or may have different angles of incidence. The angle of incidence can be normal to the surface of the substrate, or at any suitable angle from normal. In other embodiments of this invention there may be a plurality of pump and probe beams applied to the sample, within individual ones of the plurality of pump and probe beams having different angles of incidence, and/or wavelengths, and/or delay times, and/or polarizations. The plurality of pump and probe beams can be applied simultaneously and detected, by example, with an area array photodetector. By example, and for the case where different wavelengths are applied, the area array can be provided with suitable wavelength selective filters, such as dichroic filters. These and other embodiments are all within the scope of the teaching of this invention, and may furthermore be applied also to making acoustic-based measurements.

Figure 4:
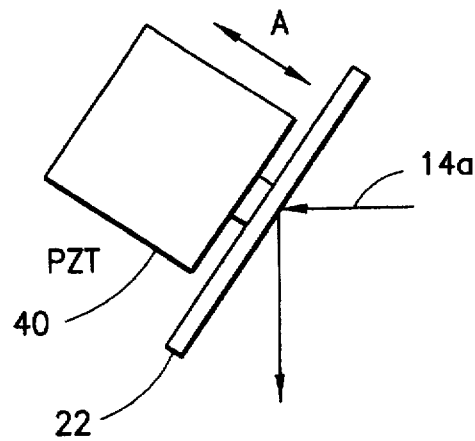
FIG. 4 illustrates an oscillating mirror which is one embodiment of a mechanism for variably delaying the probe beam with respect to the pump beam.

By example, and referring to FIG. 4, it is within the scope of the teaching of this invention to employ a piezoelectric transducer (PZT) 40 that is connected to one of the mirrors within the probe beam optical path. The PZT 40 causes a translation of the mirror, e.g., the mirror 22, along the axis labeled A. When the mirror is moving away from the probe pulse there is a gradual increase in the probe pulse optical path length and thus also in the delay between consecutive probe pulses at the surface 30a of the sample 30. In this embodiment it is assumed that the probe pulse PRR is significantly greater than the oscillation rate of the PZT/mirror assembly.

In general, the delay can be achieved through the use of a mechanical stage, such as a "shaker". A shaker is a device that vibrates a retro-reflector mirror back and forth to give, for example, a 30 psec delay oscillating at 30 Hz.

The delay can also include a double modulation. By example, there may be a mechanical stage that is swept smoothly over a large delay in conjunction with a small-amplitude, high-frequency shaker that is driven by a piezoelectric device. In this embodiment the shaker produces a time-varying delay which is a fraction of the duration of the probe pulse. In this configuration the pump need not be modulated and the lock-in amplifier is referenced to the shaker frequency.

The delay may also be achieved through the use of two lasers running at different repetition frequencies. By example, one laser operates with a repetition rate of 100.1 MHz while the second laser operates with a repetition rate of 100 MHz. In this configuration there need be no lock-in amplifier, but simply a signal averager whose time-base is synchronized to the difference frequency of the two lasers, i.e. 100 kHz.

Figure 5:
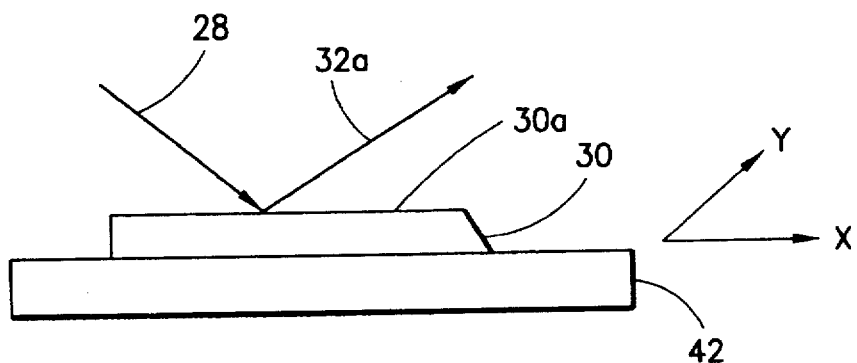
FIG. 5 illustrates an x-y stage positioning mechanism which is an embodiment of a mechanism for changing a location where the pump/probe beams intersect the surface of the sample under test.

Referring to FIG. 5, it is also within the scope of the teaching of this invention to mount the sample 30 to an x-y stage 42 for translating the surface 30a of the sample 30 with respect to the pump/probe pulses. This also enables different regions of the surface 30a to be sampled.

Figure 8A:
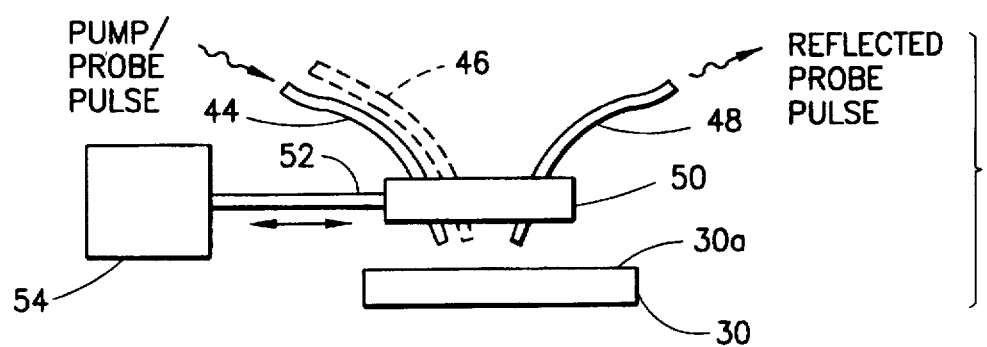
FIG. 8A illustrates a further embodiment of this invention wherein one or more optical fibers are positioned for delivering the pump beam and/or probe beam and for conveying away the reflected probe beam.

Referring to FIG. 8A, it is also within the scope of the teaching of this invention to deliver the pump pulse, or the probe pulse, or both the pump and probe pulses, through an optical fiber 44. Alternatively, a second input fiber 46 can be provided, whereby the pump pulse is delivered through the fiber 44 and the probe pulse is delivered through the fiber 46. Another fiber 48 can also be employed for receiving the reflected probe pulse and delivering same to the photodetector 34. For this embodiment the end of the optical fiber(s) are affixed to and supported by a holding stage 50. The holding stage 50 is preferably coupled through a member 52 to an actuator 54, such as a linear actuator or a two degree of freedom positioning mechanism. In this manner the reliability and repeatability of the measurement cycle is improved, in that the size and position of the focussed pump, probe, or pump and probe beams on the sample surface are independent of minor changes in the direction or profile of the laser output beams, or changes in the profile of the probe beam associated with the motion of any mechanical stage that may be used to effect the delay $t_D$. Preferably, the angular orientation between the end of the probe beam delivery fiber and the end of the reflected probe beam fiber is such as to optimize the gathering of reflected probe beam light from the surface 30a. It is also within the scope of this invention to use one or more lenses following the fiber or fibers, in order to focus the output beams from the fibers onto the sample surface, or to collect the reflected probe light and to direct it into the fiber 48 of FIG. 8A.

Figure 8B:
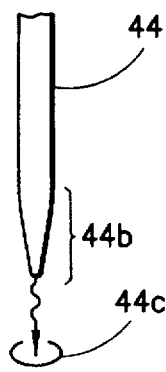
FIG. 8B illustrates a terminal end of a fiber optic that has been reduced in cross-sectional for delivering an optical pulse to a small surface area of a sample.

FIG. 8B shows an embodiment wherein a terminal portion 44b of a pump and/or probe beam delivery fiber 44a is reduced in diameter, such as by stretching the fiber, so as to provide a focussed spot 44c having a diameter that is less than the normal range of optical focussing. When coupled with the embodiment of FIG. 8A this enables the pump and or probe optical pulse to be repeatably delivered to a very small region of the surface 30a (e.g., to a spot having a diameter ≤ one micrometer), regardless of any changes that are occurring in the optical path length of the probe beam.

The graphs of FIGS. 6A and 6B present data which show that the recovery rate of the semiconductor material, after excitation, increases monotonically with increasing dosage and with increasing implant energy. The largest change in reflectivity occurs within the first few picoseconds after the application of the pump pulse.

A preferred procedure to obtain a most accurate estimate of implant dosage for an unknown test sample is as follows. First, ΔR(t) data is taken for some number of known test samples with implant levels in a range that includes the dosage level of the test sample, e.g., between $10^{10}$ cm$^{-2}$ and $5 \times 10^{10}$ cm$^{-2}$. This reference data may be stored in the data storage device 98 that is illustrated in FIG. 1B. Second, an interpolation is performed between the different known samples to find estimated curves of ΔR(t) for intermediate implant doses. Third, a comparison is made between the interpolated curves and the curve(s) obtained from an unknown sample to determine the implant dose of the unknown sample.

It should be noted that it is not required to measure the entire curve of ΔR(t) as a function of time. One can instead measure ΔR(t) at some predetermined number (e.g., three) of suitably selected times, and to carry out the analysis based on the results obtained at the selected times. By example only, and referring to FIG. 6B, it may be desirable to determine ΔR(t) only at times of 50, 100 and 150 psec, or at times of 50, 250 and 500 psec, and to interpolate the ΔR(t) curve shape from the measured points.

Data for a number of other implant species including As, Ge, Si, BF$_2$, H and P have also been obtained. In general, the forms of the curves of ΔR(t) are qualitatively similar to the results for boron as shown in FIGS. 6A–6B.

Figure 10A:
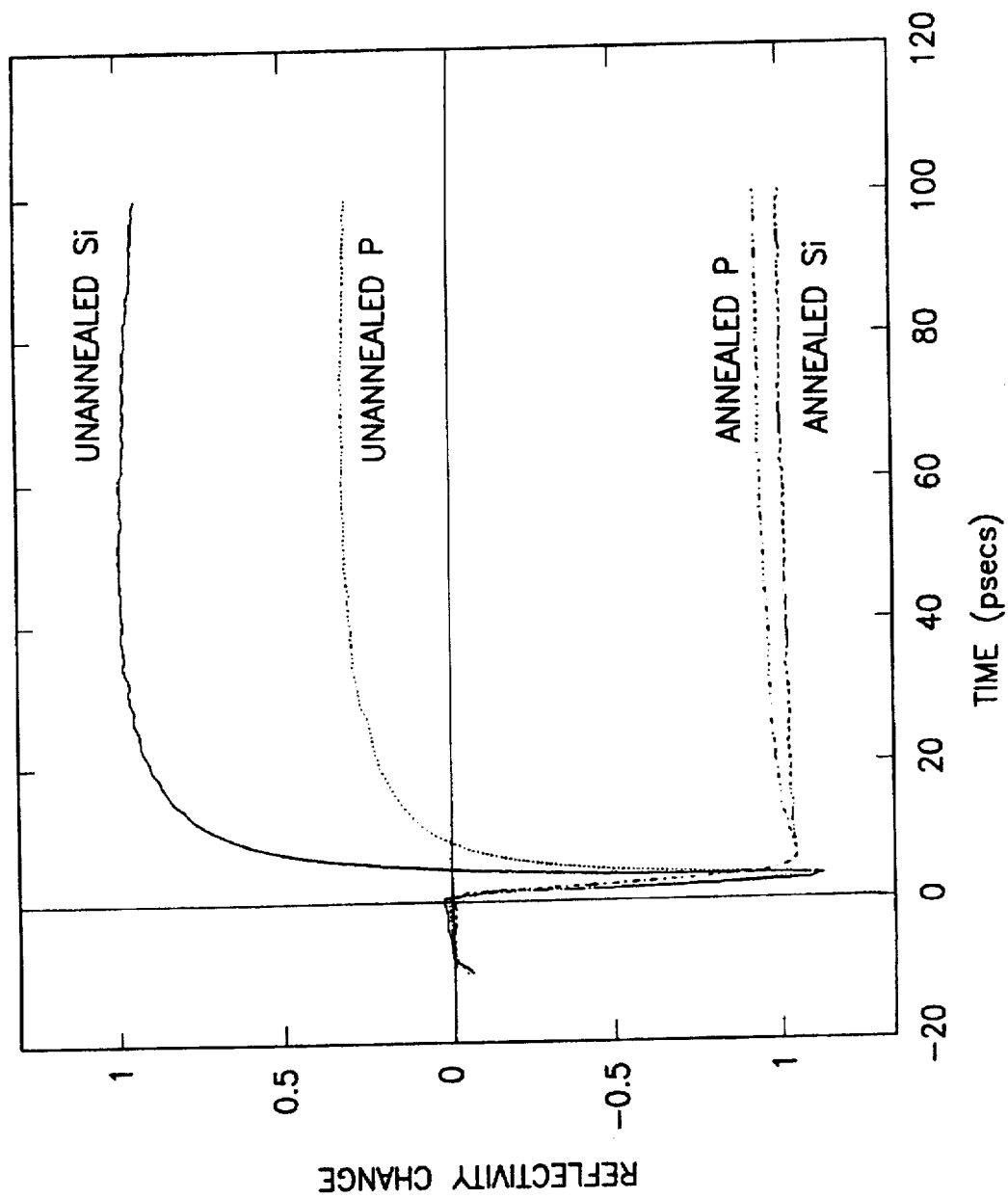
FIG. 10A is a graph illustrating a change in reflectivity over 100 picoseconds for wafers implanted with Si and P ions, before and after thermal annealing to reduce the damage caused by the implantation process.

By example, the top ΔR(t) curves in FIG. 10A illustrate data obtained with Si and P ions implanted into the surface 30a of a silicon sample 30. The dose was $10^{14}$ cm$^{-2}$ and the implant energy was 30 keV. The lower two curves show data taken for the same samples after annealing at 950° C. for 30 minutes. These measurements show that the invention can be used as a test to confirm that annealing of implant damage has been achieved.

Figure 10B:
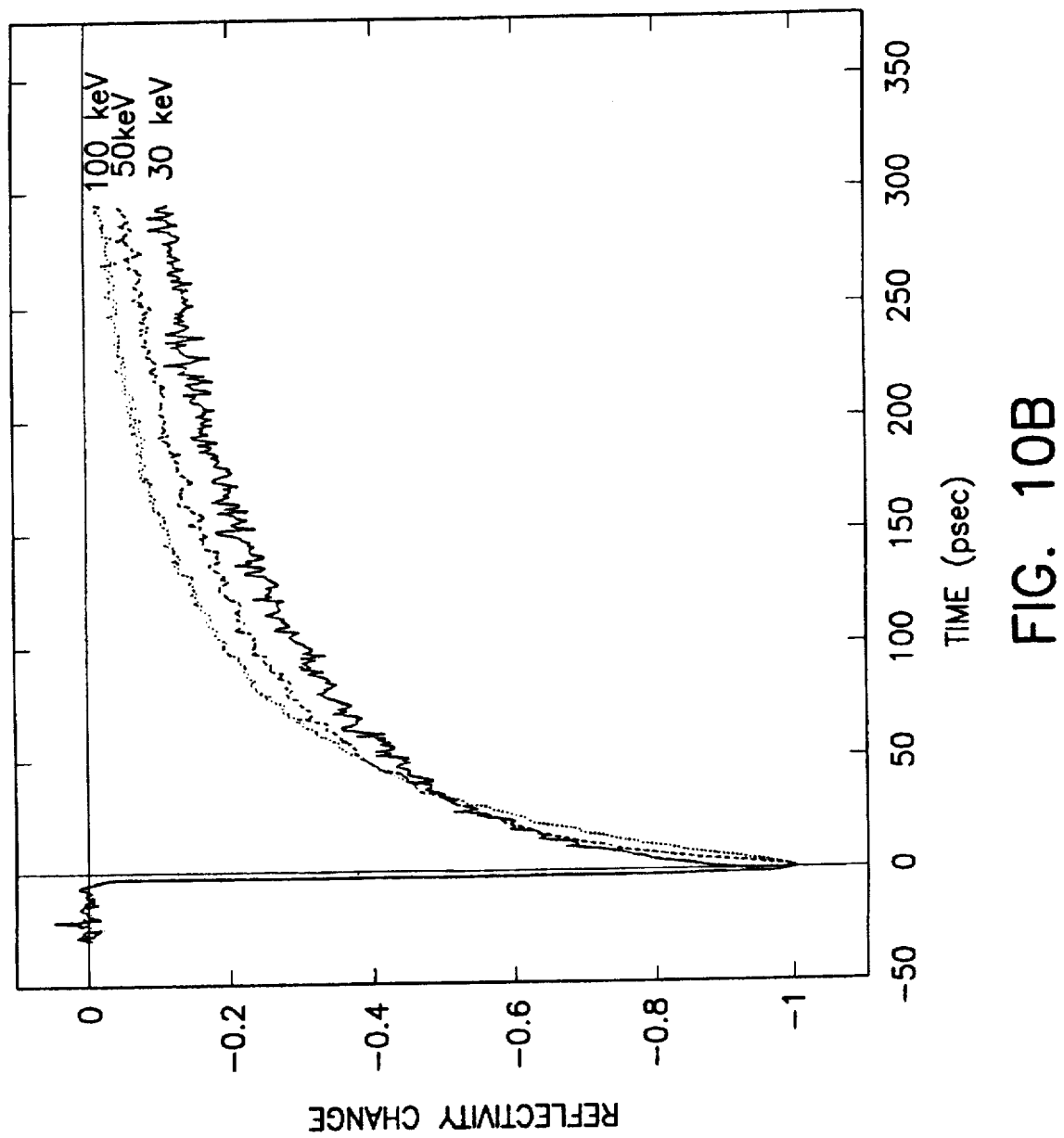
FIG. 10B is a graph illustrating a change in reflectivity over 300 picoseconds for three silicon wafers each implanted with the same dose of boron atoms but with different implant energies.

FIG. 10B illustrates an aspect of the invention wherein the implant energy can be determined from the measurement of ΔR(t). Measurements are shown for three silicon wafers implanted with B ions at a density of $10^{12}$ cm$^{-2}$. The samples were implanted at ion energies of 30, 50 and 100 kev as indicated in the figure. It should be noted that these three data sets have each been independently scaled so that the maximum change in reflectivity is normalized to have unit magnitude.

Figure 10C:
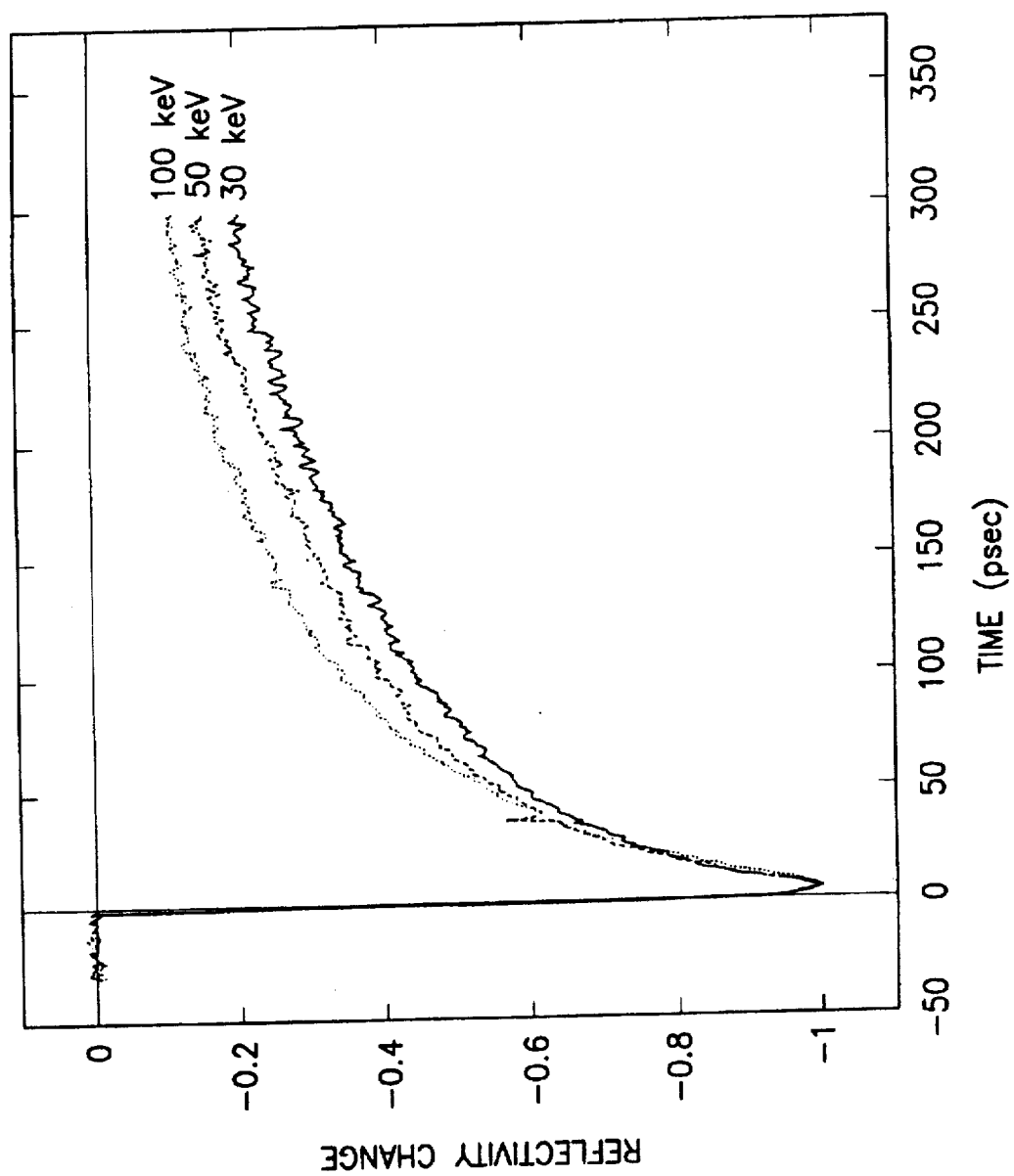
FIG. 10C is a graph illustrating a change in reflectivity over 300 picoseconds for three silicon wafers each with an overlayer of silicon dioxide, and implanted with the same dose of boron atoms but with different implant energies.

FIG. 10C illustrates an aspect of the invention wherein the implant dose can be determined through an overlying layer that does not significantly absorb the pump or probe beams. Measurements are shown for three silicon wafers implanted with B ions at a density of $10^{12}$ cm$^{-2}$. The samples were implanted at ion energies of 30, 50 and 100 keV as indicated in the figure. Each silicon sample was coated with a layer of dielectric material, specifically $SiO_2$, having a nominal thickness of approximately 220 Angstroms. As is evident, the measurement system in accordance with the teaching of this invention is capable of characterizing the implant dose through an overlying film or layer of material that does not strongly absorb the wavelength(s) of interest (e.g., a wavelength in the range of 700 to 800 nm in the present instance).

Figure 10D:
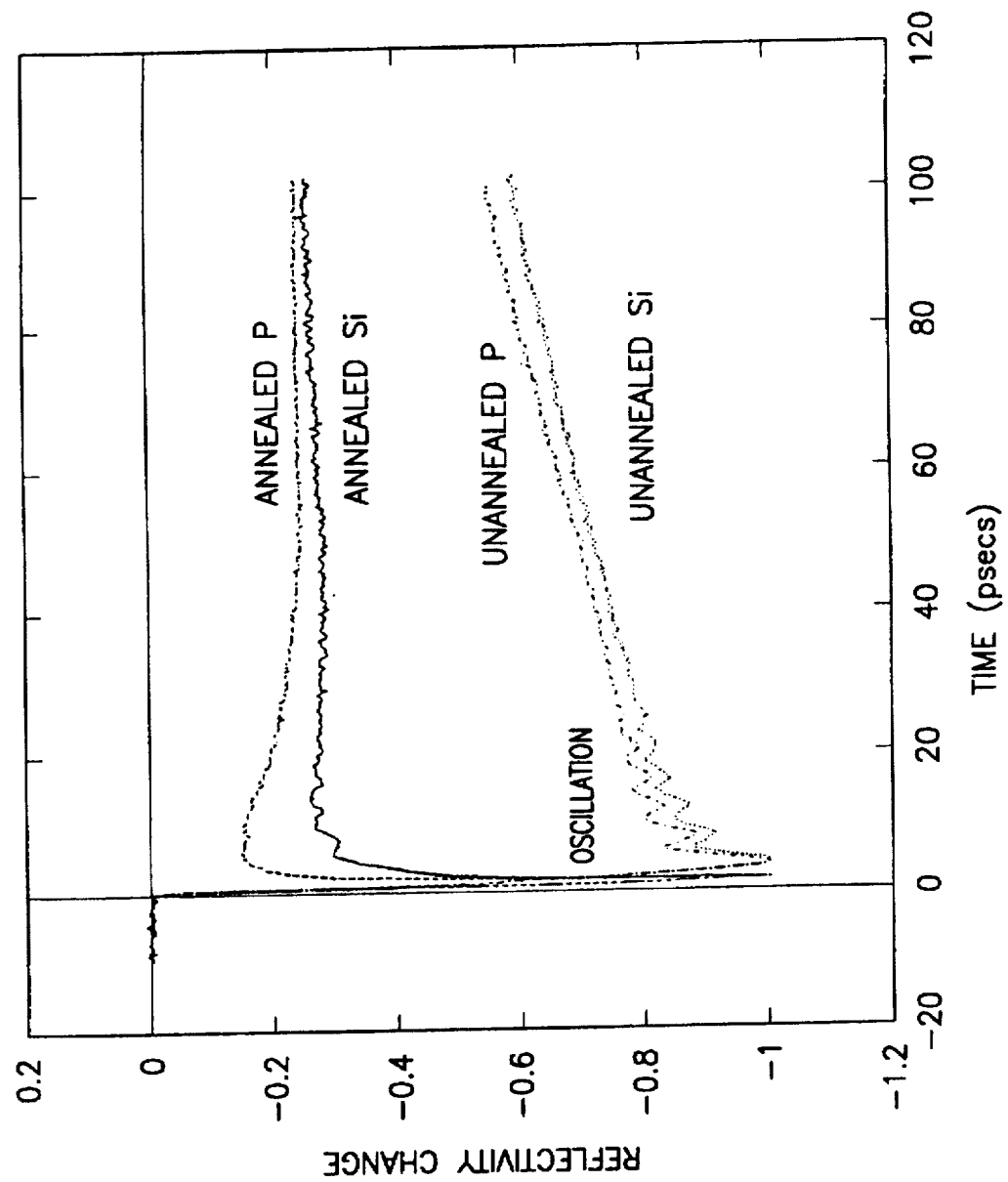
FIG. 10D is a graph illustrating a change in reflectivity over 100 picoseconds for wafers implanted with Si and P ions, before and after thermal annealing to reduce the damage caused by the implantation process, wherein the wafers studied are the same as in FIG. 10A, but the wavelengths of the pump and probe beams are reduced by a factor of approximately two; wherein in FIGS. 6A, 6B and 10A–10D the quantity plotted in the vertical direction is the reflectivity on a scale such that the maximum change is one unit.

FIG. 10A shows results obtained with the pump and the probe light having a wavelength in the range of around 750 nm. FIG. 10D illustrates data obtained from the same wafers through the use of pump and probe light of wavelength around 400 nm. In this wavelength range the optical absorption is considerably larger. The high absorption of light in the layer near the surface sets up a stress which causes a mechanical wave to be launched into the structure. As this wave propagates away from the surface it produces a local modification of the optical properties of the wafer. The probe light pulse undergoes partial reflection at the instantaneous location of the mechanical wave. The interference between the part of the probe light pulse reflected at the mechanical wave and the part of the probe light reflected at the surface of the wafer gives rise to the oscillations in $\Delta R(t)$ which can be seen in FIG. 10D. In the annealed wafers the optical absorption in the implanted region near to the wafer surface is not as large. Consequently, a weaker mechanical wave is generated and the oscillations in $\Delta R(t)$ are smaller. Thus, the determination of the strength of the oscillations provides another means to evaluate the condition of the ion-implanted layer near the surface of the wafer.

It is possible that the results for $\Delta R(t)$ for a given implant dose and energy may be affected to some extent by several other parameters. These may include the beam current per unit area during the implant process, the doping of the semiconductor material (if any), other features of the surface preparation, and the intensity of the laser pulses used for the measurement. If this is the case then it is desirable that the known samples also be prepared and/or characterized in the same or a similar manner as the unknown samples.

Figure 7A:
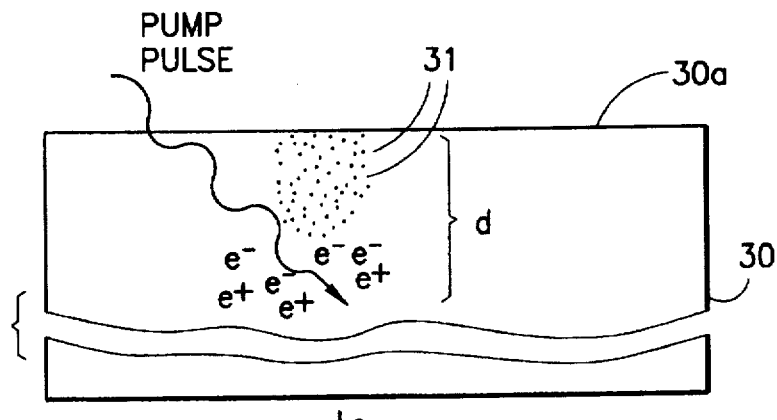
FIGS. 7A–7E are enlarged cross-sectional views, not to scale, showing the generation of charge carriers by the pump beam at time $t_0$ (FIG. 7A), the diffusion of the charge carriers at time $t_1$ (FIG. 7B), and the application of probe beams at times $t_2$ and $t_3$.

Referring to FIGS. 7A–7E, it is believed that the observed effects can be understood as follows. As is shown in FIG. 7A, a fraction of the pump pulse is absorbed in the implant region and the remainder is absorbed in the sample 30. The absorption length (d) in the sample depends on wavelength. For the wavelength range of 700 nm to 750 nm the absorption length is typically 7 micrometers for a silicon sample. The absorption of the pump pulse results in the generation of charge carriers, i.e., electrons (e$^-$) and holes (e$^+$) are generated throughout the absorption length distance. The free electrons and holes affect the optical "constants" of the semiconductor sample and result in a change in reflectivity.

Figure 7B:
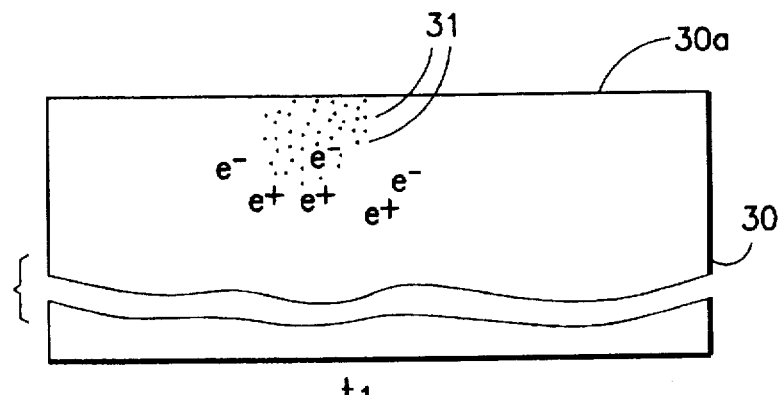

In an ion-implanted sample there is rapid recombination of the charge carriers at or near the surface 30a. FIG. 7B shows the diffusion of the charge carriers into the implanted region and into the surrounding non-implanted region of the sample. The rate at which the excited carriers are removed is determined by the rate of the surface recombination, together with the diffusion coefficients of electrons and holes in the semiconductor material. Within the implanted region the removal of the charge carriers due to recombination and trapping at defect sites will differ significantly from what occurs in the non-implanted semiconductor material.

Thus, and unlike in the report of F. E. Doany et al. referred to above, in which a thin film of a semiconducting material was studied, the charge carriers must diffuse before they can interact with the implanted ions and defects near the material's surface.

Figure 7C:
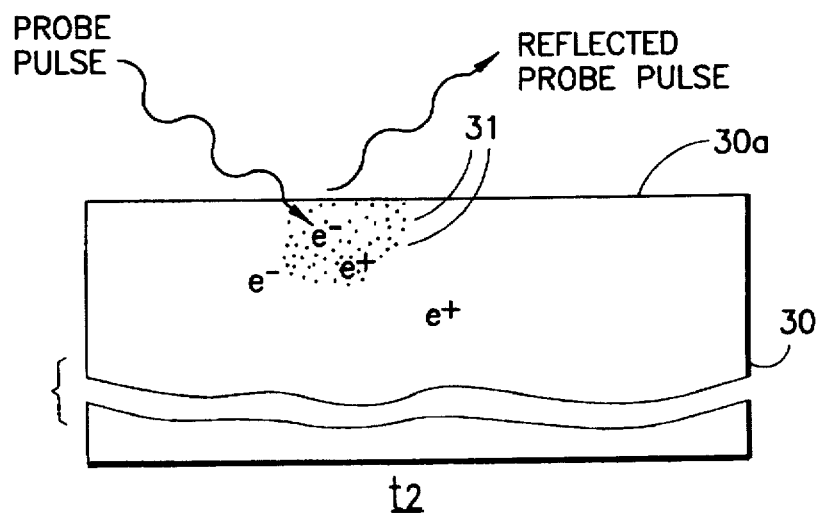
Figure 7D:
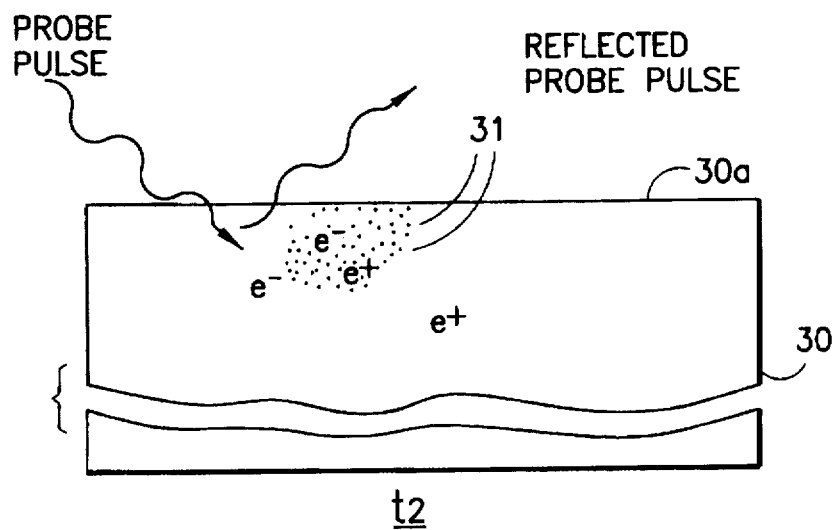
Figure 7E:
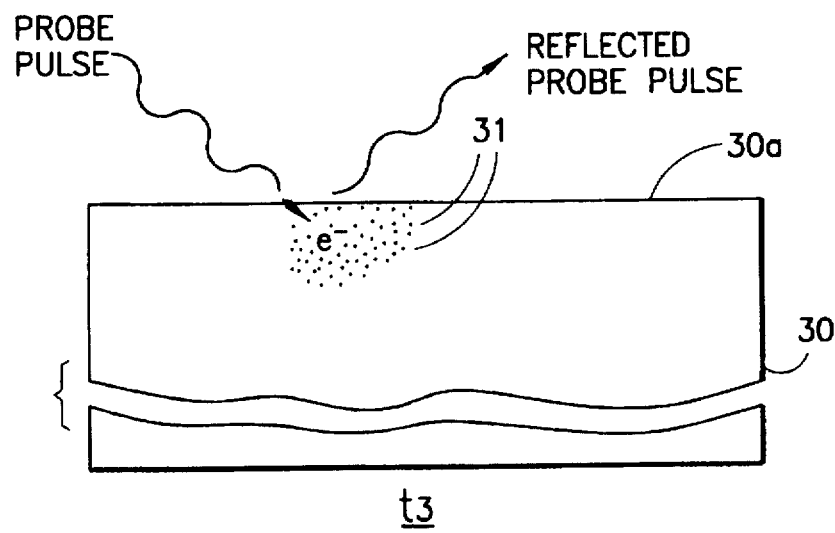
Figure 7F:
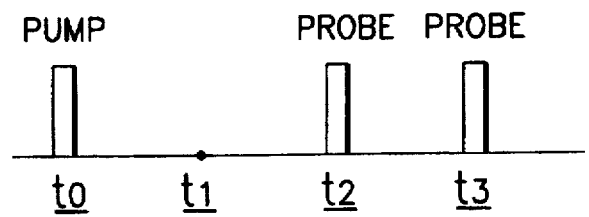
FIG. 7F is a timing diagram that relates to the sequence shown in FIGS. 7A–7E, wherein each probe pulse has a distinct pump pulse at $t_0$.

FIG. 7C illustrates a first probe pulse that arrives at time $t_2$, for example 10 picoseconds after the arrival of the pump pulse ($t_0$), and that strikes the implanted region. FIG. 7D also illustrates the first probe pulse that arrives at time $t_2$, but that strikes the non-implanted region. For this case it is clear that optical properties of the implanted and the non-implanted regions will differ, and that the resulting change in optical reflectivity of the sample to the probe beam will also differ. FIG. 7E illustrates a second probe pulse that arrives at time $t_3$, for example 20 picoseconds after the arrival of the pump pulse ($t_0$), and that strikes the implanted region. Contrasting FIGS. 7C and 7E, it can be seen that during the additional 10 picoseconds that elapse from the absorption of the pump pulse that fewer charge carriers will remain within the implanted region. The reduction in the number of charge carriers results in a corresponding, and measurable, change in the optical constants of the sample and, for example, in a time-dependent change in the reflectivity of the sample 30 to the probe beam.

This invention exploits the above-described mechanisms to measure a change in reflection, polarization, phase, etc. due to a change in optical constants over time, and to correlate this change with at least one of implant dosage, implant energy, dopant species type, the presence or absence of an implanted chemical species within a region of a sample, a level of implant-related damage, and other effects relating to the introduction of a chemical species into a sample.

Figure 9:
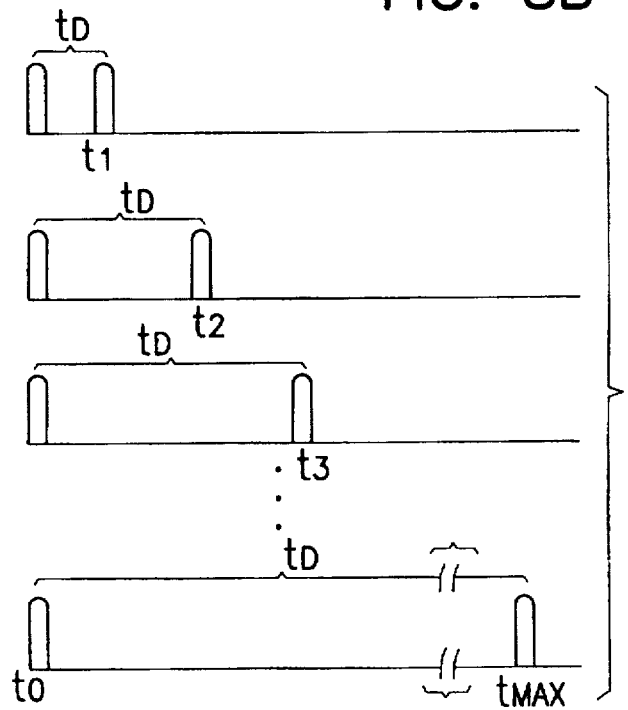
FIG. 9 illustrates a timed sequence of a plurality of consecutive pump pulses and corresponding probe pulses.

FIG. 9 makes it clear that the pump and probe pulses may be applied in pairs. That is, for each pump pulse a single probe pulse is applied to the sample to measure the change in reflectivity. By example, for a series of pump pulses each of which is defined to be applied at time $t_0$, a corresponding probe pulse is applied at different time delays ($t_D$) of $t_1$, $t_2$, $t_3$, and $t_{max}$. The spacing between pump pulses (e.g., 1/75 MHz or 13.3 nanoseconds) insures that the optical effects resulting from the previous pump pulse have become small before the application of the next pump pulse.

It is also within the scope of this invention to apply a single pump pulse, followed by two or more probe pulses. It is also within the scope of this invention to apply one or more pump pulses, and a cw or substantially cw probe beam.

It should also be apparent from FIG. 9 that this invention enables a characterization of an implanted or diffused region in a very short period of time. That is, and assuming that three probe pulses are used and that the resulting reflectivity measurements used to interpolate the $\Delta R(t)$ curve, an entire measurement cycle can be concluded in approximately 40 nanoseconds, or the time required to generate three consecutive pump pulses (and corresponding probe pulses) at a 75 MHz rate. However, so as to compensate for variations in the probe and pump optical pulses, a series of measurements are preferably taken over a longer period of time and then averaged to improve the signal-to-noise ratio.

It is within the scope of this invention to vary the wavelength of the pump and/or probe pulses during a measurement cycle, and to use other wavelengths than those in the range of 700 nm to 750 nm. A change in $\lambda$ may also reduce the data acquisition time considerably. Similarly, a reduction in the spot size on the surface 30a should also reduce the measurement time.

It is also within the scope of this invention to generate a sequence of pump pulses at a first frequency ($f_1$) and a sequence of probe pulses at a second frequency ($f_2$), wherein $f_2 \neq f_1$. In this case the signal averager 38 is triggered at a rate that is equal to $f_1 - f_2$.

In addition, the teaching of this invention is applicable to a number of different types of sample materials other than Si, including, but not limited to, Ge, the Group III-V alloy materials (e.g., GaAs, GaAlAs), and also Group II-VI alloy materials. The teaching of this invention is also not limited for use only with the specific chemical species that have been described above. Furthermore, the measurement system in accordance with the teaching of this invention is also well suited for measuring samples into which a chemical species has been diffused from a solid, liquid or gaseous source, and wherein an amount of physical damage to the sample may be negligible.

In still other embodiments of this invention the wavelength of the pump and/or probe pulsed beams can be selected or tuned to an energy level of the chemical species that has been introduced into the sample, or may be tuned to an energy transition of the sample itself, thereby enhancing sensitivity and desensitizing the measurement to surface effects.

In still other embodiments of this invention, and assuming that a photodetector having an adequate response time is available, the probe pulse can be eliminated and the photodetector used to measure a change in the optical constants of the sample that occurs during the pump pulse itself.

It should be clear that the teaching of this invention overcomes the problems inherent in the optical measurement systems that were referred to earlier. By example, the measurement system of this invention operates in the time domain and not in the frequency domain. By examining the sample over very short time scales only transient effects are considered. Even though a background equilibrium population of charge carriers may be generated over a series of pump pulses, the system of this invention examines only the transient effect induced by a most recent pump pulse, and is not specifically concerned with the dynamics of the background equilibrium population.

Furthermore, the acoustic techniques of Tauc et al. can be employed as an adjunct to the measurement system in accordance with this invention. By example, the acoustic technique can be employed to measure the depth of an implanted region, while the measurement technique of this invention can be employed to determine the density of the implanted species.

By a further example, the top $\Delta R(t)$ curves in FIG. 10D illustrate data obtained with Si and P ions implanted into the source 30a of a silicon sample 30. The dose was $10^{14}$ cm$^{-2}$ and the implant energy was 30 keV. The lower two curves show data taken for the same samples after annealing at 950° C. for 30 minutes. These measurements were made using pump and probe light pulses of wavelength 400 nm. As was described previously, at this short wavelength the light is strongly absorbed in a layer near to the surface and a stress is set up in this region. This stress launches a strain pulse into the interior of the wafer. This strain causes a local change in the optical properties of the silicon. When the probe light pulse passes through the region containing the strain pulse it is partially reflected. The interference between this reflected component of the probe light and the part of the probe light reflected at the surface of the silicon wafer gives rise to the oscillations in optical reflectivity which can be seen in FIG. 10D. The magnitude and also the frequency of these oscillations can be used as a probe of the ion density and of the extent to which the damage has been annealed.

It should further be realized that while the wavelength of the pump radiation should be suitable for generating electrons and holes in the semiconductor sample, the wavelength of the probe radiation is not so constrained.

The teaching of this invention has thus been described in the context of apparatus and methods for inducing at least one transient time-dependent change in the optical constants n and κ of a sample in a region close to the surface of the sample, and also in a displacement of the surface. These changes lead to a change $\Delta R(t)$ in the optical reflectivity, a shift $\delta\phi(t)$ in the phase of the reflected or transmitted light, a change in the polarization state of the reflected light, and a change in direction of the reflected or transmitted light. These changes are dependent also on the polarization and the angle of incidence of the probe light. The measured changes in the response of the sample to light depend, among other things, on the distribution of defects and foreign atom species near the sample's surface and in the bulk. The measured changes are associated with at least one of species concentration, species type, implant energy, the presence or absence of an introduced-species region within the location, and a presence or absence of implant-related damage.

Furthermore, and although described in the context of apparatus and methods that employ curves obtained from one or more reference samples, it is also within the scope of this invention to employ the computer 96 of FIG. 1B to compare a measured or generated curve to a reference curve calculated from a theoretical model of the sample and the introduced chemical species.

Thus, while the invention has been particularly shown and described with respect to preferred embodiments thereof, it will be understood by those skilled in the art that changes in form and details may be made therein without departing from the scope and spirit of the invention.

What is claimed is:

1. Apparatus for examining a semiconductor sample having at least one localized region underlying a surface into which a chemical species may have been introduced, comprising:

optical means for generating optical pump pulses having a wavelength selected for generating a population of charge carriers in said sample, said charge carriers diffusing within and recombining in said sample and said localized region and inducing at least one transient time-varying change in optical constants of the sample at a location at or near to the surface of the sample, said optical means further being operable for generating an optical probe beam;

means for measuring a response of the sample to said optical probe beam at least during a time that the optical constants are varying; and means for associating the measured response with at least one of chemical species concentration, chemical species type, implant energy, a presence or absence of an introduced chemical species region at the location, and a presence or absence of implant-related damage.

2. Apparatus as set forth in claim 1, wherein said optical means is comprised of means for generating probe beam pulses.

3. Apparatus as set forth in claim 1, wherein said optical means is comprised of means for generating a continuous wave probe beam.

4. Apparatus as set forth in claim 1, wherein said pump beam pulses each have a duration in a range of approximately 0.01 picosecond to approximately 100 picoseconds, an energy of approximately 0.001 nJ to approximately 100 nJ per pulse, and a wavelength that is equal to approximately 200 nm or greater.

5. Apparatus as set forth in claim 1, wherein said measuring means is comprised of a detector that is positioned for receiving said optical probe beam after it impinges on the sample, and wherein said measuring means is further comprised of means for measuring a change in reflected intensity of the probe beam.

6. Apparatus as set forth in claim 1, wherein said measuring means is comprised of a detector that is positioned for receiving the probe beam after it impinges on the sample, and wherein said measuring means is further comprised of means for measuring a change in transmitted intensity of the probe beam.

7. Apparatus as set forth in claim 1, wherein said measuring means is comprised of a detector that is positioned for receiving the probe beam after it impinges on the sample, and wherein said measuring means is further comprised of means for measuring a change in a polarization state of the probe beam.

8. Apparatus as set forth in claim 1, wherein said measuring means is comprised of a detector that is positioned for receiving the probe beam after it impinges on the sample, and wherein said measuring means is further comprised of means for measuring a change in optical phase of the probe beam.

9. Apparatus as set forth in claim 1, wherein said measuring means is comprised of a detector that is positioned for receiving the probe beam after it impinges on the sample, and wherein said measuring means is further comprised of means for measuring a change in direction of the probe beam.

10. Apparatus as set forth in claim 1, wherein said measuring means is comprised of a detector that is positioned for receiving the probe beam after it impinges on the sample, and wherein said measuring means is further comprised of means for measuring a change in optical path length between the surface and the detector.

11. Apparatus as set forth in claim 1, wherein said optical means applies a plurality of pairs of optical pulses to the sample, each of the pairs of pulses comprising an optical pump pulse and an optical probe pulse, said probe pulse being delayed in time from said pump pulse by a delay time $t_D$, wherein for at least some of the pairs of pulses $t_D$ is less than a charge carrier recombination time within the sample.

12. Apparatus as set forth in claim 11, and further comprising mechanical means for generating the time delay $t_D$.

13. Apparatus as set forth in claim 12, wherein the mechanical means is comprised of a piezoelectric transducer that is coupled to a mirror that reflects said probe pulses.

14. Apparatus as set forth in claim 12, wherein the mechanical means is comprised of a shaker table that is coupled to a mirror that reflects said probe pulses.

15. Apparatus as set forth in claim 1, wherein said associating means is comprised of a digital data processor, wherein said digital data processor generates a curve that is a function of a change in the optical constants over time, and wherein said digital data processor compares the generated curve to at least one reference curve obtained from at least one reference sample.

16. Apparatus as set forth in claim 1, wherein said associating means is comprised of a digital data processor, wherein said digital data processor generates a curve that is indicative of a change in the optical constants over time, and wherein said digital data processor compares the generated curve to at least one reference curve that is calculated from a model of the sample.

17. Apparatus as set forth in claim 1, wherein said optical means generates a sequence of pump pulses at a frequency of $f_1$, the sequence of pump pulses being intensity modulated at a frequency of $f_2$, and wherein $f_2 < f_1$.

18. Apparatus as set forth in claim 1, wherein said optical means generates a sequence of pump pulses at a frequency of $f_1$ and a sequence of probe pulses at a frequency of $f_2$, and wherein $f_2 \neq f_1$.

19. Apparatus as set forth in claim 1, wherein said optical means applies at least one of a pump pulse and a probe pulse to the surface through an optical fiber.

20. Apparatus as set forth in claim 1, wherein said measuring means includes an optical fiber for directing a reflected probe pulse to a photodetector.

21. Apparatus as set forth in claim 1, wherein said optical means is comprised of means for focussing a pump pulse and a probe pulse onto the surface, and wherein said focussing means is comprised of an optical fiber having a terminal end portion that is reduced in diameter over other portions of the optical fiber.

22. Apparatus as set forth in claim 1, wherein said optical means is comprised of a laser for generating optical pulses at a rate within a range of approximately 100 pulses per second to approximately $5 \times 10^9$ pulses per second.

23. Apparatus as set forth in claim 1, wherein said optical means is comprised of a single laser for generating an optical pump pulse and an optical probe pulse.

24. Apparatus as set forth in claim 1, wherein said optical means is comprised of a first laser for generating an optical pump pulse and a second laser for generating an optical probe pulse.

25. Apparatus as set forth in claim 1, wherein said optical means generates, for each optical pump pulse, a plurality of optical probe pulses.

26. Apparatus as set forth in claim 1, wherein said measurement means obtains measurements as a function of an amplitude of said optical pump pulses.

27. Apparatus as set forth in claim 1, wherein said optical means generates optical probe pulses, and wherein said optical pump pulses and said optical probe pulses are applied at an angle normal to said surface.

28. Apparatus as set forth in claim 1, wherein said optical means generates optical probe pulses, and wherein said optical pump pulses and said optical probe pulses are applied at an angle other than normal to said surface.

29. Apparatus as set forth in claim 1, wherein said optical means generates optical probe pulses, and wherein said optical pump pulses and said optical probe pulses are applied along a same axis to said surface.

30. Apparatus as set forth in claim 1, wherein said optical means generates optical probe pulses, and wherein said optical pump pulses and said optical probe pulses are applied along two different axes to said surface.

31. Apparatus as set forth in claim 1, wherein said optical means generates optical probe pulses, and wherein said optical pump pulses and said optical probe pulses are applied to a same location on said surface.

32. Apparatus as set forth in claim 1, wherein said optical means generates optical probe pulses, and wherein said optical pump pulses and said optical probe pulses are applied to two different locations on said surface.

33. Apparatus as set forth in claim 1, wherein said optical means generates optical probe pulses having a predetermined polarization state, and wherein said measuring means includes means for detecting ellipsometric parameters upon a reflection or transmission of said optical probe pulses.

34. Apparatus as set forth in claim 1, wherein said optical means generates sets of pump/probe pulses each comprising at least one optical pump pulse and at least one optical probe pulse, and wherein said measuring means includes means for detecting, from an oscillation in a change in at least one of intensity, polarization state, and optical phase of light reflected from or transmitted through said sample, at least an indication of an amount of lattice defects present in the sample.

35. A method for examining a semiconductor sample having at least one localized region underlying a surface into which a chemical species may have been introduced, comprising the steps of:

generating optical pump pulses having a wavelength selected for generating a population of charge carriers in the sample, the charge carriers diffusing within and recombining in the sample and the localized region and inducing at least one transient time-varying change in optical constants of the sample at a location at or near to a surface of the sample;

measuring a response of the sample to an optical probe beam at least during a time that the optical constants are varying; and associating the measured response with at least one of chemical species concentration, chemical species type, implant energy, a presence or absence of an introduced chemical species region at the location, and a presence or absence of implant-related damage.

36. A method as set forth in claim 35, wherein the step of measuring includes a step of generating at least one of a continuous wave probe beam and a pulsed probe beam.

37. A method as set forth in claim 35, wherein the step of generating includes a step of generating pump beam pulses having a duration in a range of approximately 0.01 picosecond to approximately 100 picoseconds, an energy of approximately 0.001 nJ to approximately 100 nJ per pulse, and a wavelength that is equal to approximately 200 nm or greater.

38. A method as set forth in claim 35, wherein the step of measuring employs a detector that is positioned for receiving the optical probe beam after it impinges on the sample, and further comprising a step of measuring a change in reflected intensity of the probe beam.

39. A method as set forth in claim 35, wherein the step of measuring employs a detector that is positioned for receiving the optical probe beam after it impinges on the sample, and further comprising a step of measuring a change in transmitted intensity of the probe beam.

40. A method as set forth in claim 35, wherein the step of measuring employs a detector that is positioned for receiving the optical probe beam after it impinges on the sample, and further comprising a step of measuring a change in a polarization state of the probe beam.

41. A method as set forth in claim 35, wherein the step of measuring employs a detector that is positioned for receiving the optical probe beam after it impinges on the sample, and further comprising a step of measuring a change in optical phase of the probe beam.

42. A method as set forth in claim 35, wherein the step of measuring employs a detector that is positioned for receiving the optical probe beam after it impinges on the sample, and further comprising a step of measuring a change in direction of the probe beam.

43. A method as set forth in claim 35, wherein the step of measuring employs a detector that is positioned for receiving the optical probe beam after it impinges on the sample, and further comprising a step of measuring a change in optical path length between the surface and the detector.

44. A method as set forth in claim 35, wherein the steps of generating and measuring include a step of applying a plurality of pairs of optical pulses to the sample, each of the pairs of pulses comprising an optical pump pulse an optical probe pulse, the probe pulse being delayed in time from the pump pulse by a delay time $t_D$, wherein for at least some of the pairs of pulses $t_D$ is less than a charge carrier recombination time within the sample.

45. A method as set forth in claim 35, wherein the step of measuring includes a step of generating a curve that is a function of a change in the optical constants over time, and wherein the step of associating includes a step of comparing the generated curve to at least one reference curve obtained from at least one reference sample.

46. A method as set forth in claim 35, wherein the step of measuring includes a step of generating a curve that is indicative of a change in the optical constants over time, and wherein the step of associating includes a step of comparing the generated curve to at least one reference curve that is calculated from a model of the sample.

47. A method as set forth in claim 35, wherein the step of measuring includes a step of generating, for each optical pump pulse, a plurality of optical probe pulses.

48. A method as set forth in claim 35, wherein the step of measuring obtains measurements as a function of an amplitude of the optical pump pulses.

49. A method as set forth in claim 35, wherein the step of measuring includes a step of generating optical probe pulses having a predetermined polarization state, and wherein the step of measuring means includes a step of detecting ellipsometric parameters upon a reflection or transmission of the optical probe pulses.

50. A method as set forth in claim 35, wherein the step of measuring includes a step of detecting, from an oscillation in a change in at least one of intensity, polarization state, and optical phase of light reflected from or transmitted through said sample, at least an indication of an amount of lattice defects present in the sample.

51. A method as set forth in claim 35, wherein the surface underlies at least one layer comprised of a semiconductor material or a dielectric material.

52. A method as set forth in claim 35, wherein the step of generating includes a step of generating a sequence of pump pulses at a frequency of $f_1$, the sequence of pump pulses being intensity modulated at a frequency of $f_2$, and wherein $f_2 < f_1$.

53. A method as set forth in claim 35, wherein the step of generating includes a step of generating a sequence of pump pulses at a frequency of $f_1$, wherein the step of measuring includes a step of generating a sequence of probe pulses at a frequency of $f_2$, and wherein $f_2 \neq f_1$.

54. A method as set forth in claim 35, wherein at least one of the steps of generating and measuring includes a step of applying an optical beam to the surface through an optical fiber.

55. A method as set forth in claim 35, wherein the step of measuring includes a step of applying a reflected probe pulse to a photodetector through an optical fiber.

56. A method as set forth in claim 35, wherein at least one of the steps of generating and measuring includes a step of applying a focussed optical beam to the surface, wherein the optical beam is focussed with an optical fiber having a terminal end portion that is reduced in diameter over other portions of the optical fiber.

57. A method as set forth in claim 35, wherein at least one of the steps of generating and measuring includes a step of operating a laser for generating optical pulses at a rate within a range of approximately 100 pulses per second to approximately $5 \times 10^9$ pulses per second.

58. A method as set forth in claim 35, wherein the step of measuring includes a step of generating optical probe pulses, and wherein the optical pump pulses and the optical probe pulses are generated with a single laser.

59. A method as set forth in claim 35, wherein the step of generating generates the optical pump pulses with a first laser, and wherein the step of measuring includes a step of generating at least one optical probe beam with a second laser.

60. A method as set forth in claim 35, wherein the optical pump pulses and the optical probe beam are applied to the surface at an angle normal to the surface.

61. A method as set forth in claim 35, wherein the optical pump pulses and the optical probe beam are applied to the surface at an angle that is other than normal to the surface.

62. A method as set forth in claim 35, wherein the optical pump pulses and the optical probe beam are applied to the surface along the same axis.

63. A method as set forth in claim 35, wherein the optical pump pulses and the optical probe beam are applied to the surface along two different axes.

64. A method as set forth in claim 35, wherein the optical pump pulses and the optical probe beam are applied to a same location on the surface.

65. A method as set forth in claim 35, wherein the optical pump pulses and the optical probe beam are applied to two different locations on the surface.

66. A method as set forth in claim 35, wherein the measuring includes a step of generating the optical probe beam, and further comprising a step of varying a wavelength of the optical pump pulses and the optical probe beam.

67. A method as set forth in claim 35, wherein the step of generating includes a step of simultaneously generating a plurality of optical pump pulses each having an energy sufficient to generate charge carriers within the sample, and wherein the step of measuring includes a step of simultaneously generating a plurality of optical probe beams.

68. A method as set forth in claim 35, wherein the step of measuring includes a step of generating a plurality of optical probe beams, and wherein individual ones of the plurality of pump pulses and probe beams are generated to have at least one of different angles of incidence, different wavelengths, different delay times, and different polarizations.

69. A method for examining a semiconductor sample having at least one localized region underlying a surface into which a chemical species has been implanted, comprising the steps of:

thermally annealing the sample to reduce or eliminate implant-related damage;

generating optical pump pulses having a wavelength selected for generating a population of charge carriers in the sample, the charge carriers diffusing in the sample and localized region and recombining at different rates in the sample and the localized region, the charge carriers inducing at least one transient time-varying change in optical constants of the sample at a location at or near to a surface of the sample;

measuring a response of the sample to an optical probe beam at least during a time that the optical constants are varying; and determining, in accordance with the measured response, whether the sample has been sufficiently thermally annealed to reduce or eliminate the implant-related damage.

70. A method for examining a semiconductor sample having at least one localized region underlying a surface into which a chemical species has been implanted, comprising the steps of:

generating optical pump pulses having a wavelength selected for generating a population of charge carriers in the sample, the charge carriers diffusing in the sample and localized region and recombining at different rates in the sample and the localized region, the charge carriers inducing at least one transient time-varying change in optical constants of the sample at a location at or near to a surface of the sample;

measuring a response of the sample to an optical probe beam at least during a time that the optical constants are varying; and determining, in accordance with the measured response, an energy at which the chemical species was implanted.

71. A method for examining a semiconductor sample having at least one region underlying a surface into which a chemical species has been implanted, comprising the steps of:

generating optical pump pulses having a wavelength selected for generating a population of charge carriers in the sample, the charge carriers diffusing in the sample and localized region and recombining at different rates in the sample and the localized region, the charge carriers inducing at least one transient time-varying change in optical constants of the sample at a location at or near to a surface of the sample, individual ones of the optical pump pulses also launching a propagating mechanical wave in the sample;

measuring a response of the sample to an optical probe beam at least during a time that the optical constants are varying, the measured response including an oscillatory component due to the propagating mechanical wave; and determining, in accordance with the measured response, at least one characteristic associated with the implanted region.

* * * * *